United States Patent [19]

Packard et al.

[11] Patent Number: 5,640,995
[45] Date of Patent: Jun. 24, 1997

[54] ELECTROFLUIDIC STANDARD MODULE AND CUSTOM CIRCUIT BOARD ASSEMBLY

[75] Inventors: Warren J. Packard, Chicago, Ill.; John H. Jerman, Palo Alto, Calif.

[73] Assignee: Baxter International Inc., Deerfield, Ill.

[21] Appl. No.: 404,301

[22] Filed: Mar. 14, 1995

[51] Int. Cl.$^6$ ................................................ F16K 27/00
[52] U.S. Cl. ........................ 137/597; 137/884; 251/129.01
[58] Field of Search .................................. 137/884, 597; 251/129.01

[56] References Cited

U.S. PATENT DOCUMENTS

| | | | |
|---|---|---|---|
| 3,389,305 | 6/1968 | Bond | 317/100 |
| 3,457,943 | 7/1969 | Kawabata | 137/269 |
| 3,536,875 | 10/1970 | Allen | 200/83 |
| 3,547,139 | 12/1970 | van Berkum | 137/81.5 |
| 3,548,849 | 12/1970 | Purcell et al. | 137/81.5 |

(List continued on next page.)

FOREIGN PATENT DOCUMENTS

| | | |
|---|---|---|
| 0518524 | 12/1992 | European Pat. Off. . |
| 8514741 | 11/1987 | Germany . |

OTHER PUBLICATIONS

PCT Search Report: PCT/US96/01246 (Corresponds to U.S. Serial No. 08/404,301).
Redwood MicroSystems, Inc. data sheet (2 pages), undated, "MiniPR Pressure Regulator—Closed-Loop Pressure Control Using Fluistor™ Microvalves", no date.
Redwood MicroSystems, Inc. data sheet (2 pages), undated, "NC-1500 Fluistor™ Microvalve—Normally Closed Gas Valve", no date.
"A Valve On A Chip?" by Lyle H. McCarty, Contributing Editor, pp. 111–112 in *Design News*, dated Jan. 20, 1992.
*Design News*, Dec. 5, 1994, p. 18 "Hot Products" and Clippard Fluid Power advertisement on reverse side thereof.
Brochure and Performance Specifications (2 pages) (undated) for ICSensors, Inc. Model 4425 Microvalve.
Product: Lee Company Model No. TFDA0629202Z barbed fitting no date.
Product: T08 can-mounted valve with electrical lead wires and plastic tubing connectors no date.
Product: Fujikura of Japan Model No. FPM-15PG micromachined pressure transducer no date.
Product: SMC Model No. NVJ124A miniaturized, solenoid valves mounted on manifold block no date.
Product: Lee Company Ser. No. LHDX0500700AA very small tubular solenoid actuated valve mounted on manifold block no dated.
Product: IC Sensors Model No. ICS 4425 valve inlet, mounted in plastic package, with electrical and fluidic connectors no date.
Product: Redwood Systems "FLUISTOR™" valve mounted on printed circuit board, with electrical and fluidic connectors no date.

*Primary Examiner*—Stephen M. Hepperle
*Attorney, Agent, or Firm*—F. C. Kowalik; Fitch, Even, Tabin & Flannery

[57] ABSTRACT

A miniature electrofluidic module is disclosed, for receiving one or more fluids and for receiving an electrical connection. In accordance with one aspect of the invention, the module includes a substantially flat fluidic manifold layer for fluid distribution, a substantially flat electrical layer including an electrical circuit, and a substantially flat device layer including micromachined devices. The devices may include electrically actuated valves for modulating the flow of fluids. In another aspect of the invention, an electrofluidic module is combined with an electrofluidic circuit board. In a further aspect, an electrofluidic system such as a dialysate handling system is disclosed, including a fluidic fixture and an electrofluidic assembly incorporating electrofluidic devices. In a still further aspect of the invention, a method is disclosed for interfacing micromachined devices to electrical and fluidic interfaces on a fixture, including packaging the devices into a module and providing electrical and fluidic interfaces between the module and the fixture.

37 Claims, 12 Drawing Sheets

U.S. PATENT DOCUMENTS

| | | | |
|---|---|---|---|
| 3,646,963 | 3/1972 | Klee | 137/608 |
| 3,760,844 | 9/1973 | Olson et al. | 137/608 |
| 3,766,935 | 10/1973 | Clippard, III | 137/269 |
| 3,786,831 | 1/1974 | Clippard, III | 137/269 |
| 3,814,126 | 6/1974 | Klee | 137/608 |
| 3,845,258 | 10/1974 | Bruels | 200/81 H |
| 3,895,648 | 7/1975 | Stoll et al. | 137/550 |
| 3,990,468 | 11/1976 | Arvin et al. | 137/269 |
| 4,093,329 | 6/1978 | Asbill, III | 339/16 R |
| 4,095,863 | 6/1978 | Hardin | 339/15 |
| 4,095,864 | 6/1978 | Hardin | 339/15 |
| 4,165,139 | 8/1979 | Asbill, III | 339/15 |
| 4,345,612 | 8/1982 | Koni et al. | 137/101.9 |
| 4,458,841 | 7/1984 | Laakaniemi et al. | 236/49 |
| 4,469,128 | 9/1984 | Petrimaux et al. | 137/554 |
| 4,507,707 | 3/1985 | Willis | 361/380 |
| 4,549,248 | 10/1985 | Stoll | 361/400 |
| 4,629,926 | 12/1986 | Siegal | 310/331 |
| 4,771,204 | 9/1988 | Siegal | 310/330 |
| 4,778,451 | 10/1988 | Kamen | 604/67 |
| 4,808,161 | 2/1989 | Kamen | 604/67 |
| 4,815,496 | 3/1989 | Nishitani et al. | 137/884 |
| 4,816,019 | 3/1989 | Kamen | 604/65 |
| 4,821,997 | 4/1989 | Zdeblick | 251/11 |
| 4,826,482 | 5/1989 | Kamen | 604/67 |
| 4,842,021 | 6/1989 | Stoll | 137/994 |
| 4,869,282 | 9/1989 | Sittler et al. | 137/15 |
| 4,898,360 | 2/1990 | Von Hayn et al. | 251/129.01 |
| 4,964,273 | 10/1990 | Nash | 60/325 |
| 4,976,162 | 12/1990 | Kamen | 73/865.9 |
| 5,000,226 | 3/1991 | Stoll et al. | 137/884 |
| 5,069,419 | 12/1991 | Jerman | 251/11 |
| 5,088,515 | 2/1992 | Kamen | 137/15 |
| 5,094,268 | 3/1992 | Morel et al. | 137/560 |
| 5,099,884 | 3/1992 | Monahan | 137/827 |
| 5,144,982 | 9/1992 | Willbanks | 137/625.5 |
| 5,176,359 | 1/1993 | Leveson et al. | 251/61.1 |
| 5,178,190 | 1/1993 | Mettner | 137/625.65 |
| 5,180,623 | 1/1993 | Ohnstein | 428/209 |
| 5,186,713 | 2/1993 | Raible . | |
| 5,207,642 | 5/1993 | Orkin et al. | 604/86 |
| 5,222,524 | 6/1993 | Sekler et al. | 137/884 |
| 5,234,033 | 8/1993 | Stoll et al. | 137/884 |
| 5,234,608 | 8/1993 | Duff . | |
| 5,236,665 | 8/1993 | Mathewson et al. . | |
| 5,271,597 | 12/1993 | Jerman | 251/11 |
| 5,284,179 | 2/1994 | Shikida et al. | 37/334 |
| 5,322,258 | 6/1994 | Bosch et al. | 251/65 |
| 5,324,422 | 6/1994 | Colleran et al. | 210/85 |
| 5,325,880 | 7/1994 | Johnson et al. | 137/1 |
| 5,328,559 | 7/1994 | Jerman | 156/647 |
| 5,329,965 | 7/1994 | Gordon | 137/599 |
| 5,338,400 | 8/1994 | Jerman | 156/647 |
| 5,348,047 | 9/1994 | Stoll et al. | 137/554 |
| 5,350,357 | 9/1994 | Kamen et al. | 604/29 |
| 5,364,364 | 11/1994 | Kasvikis et al. . | |
| 5,370,612 | 12/1994 | Maeda et al. . | |
| 5,417,235 | 5/1995 | Wise et al. | 137/1 |

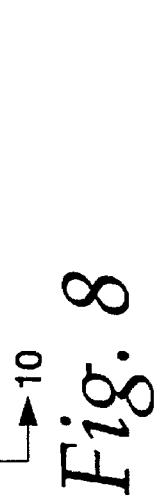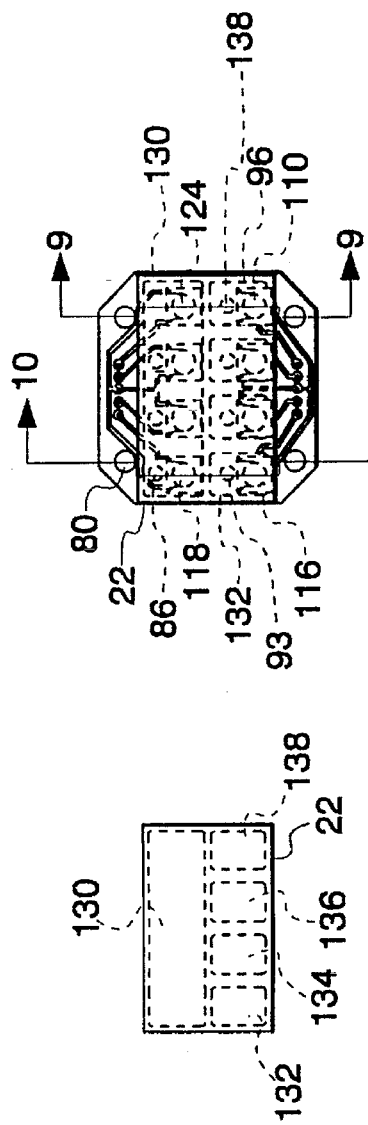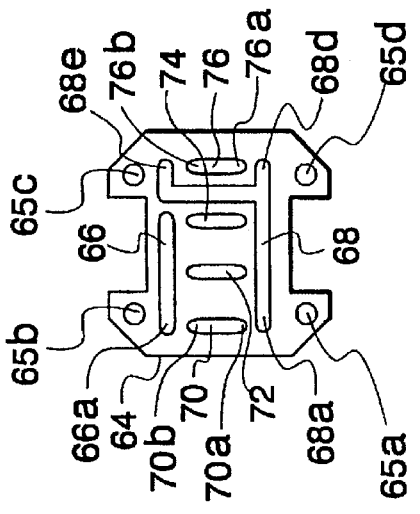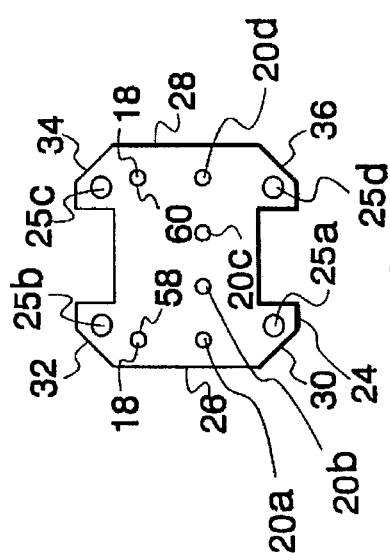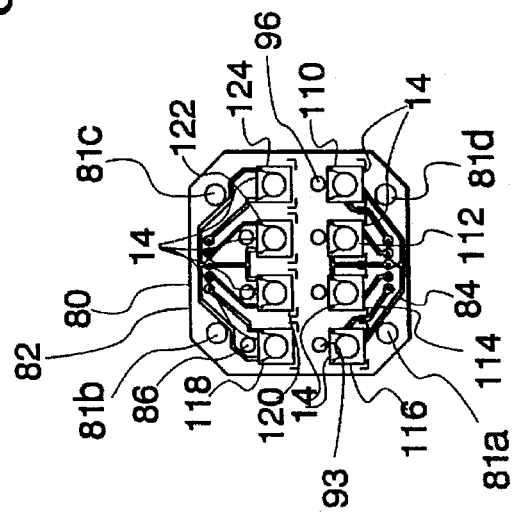

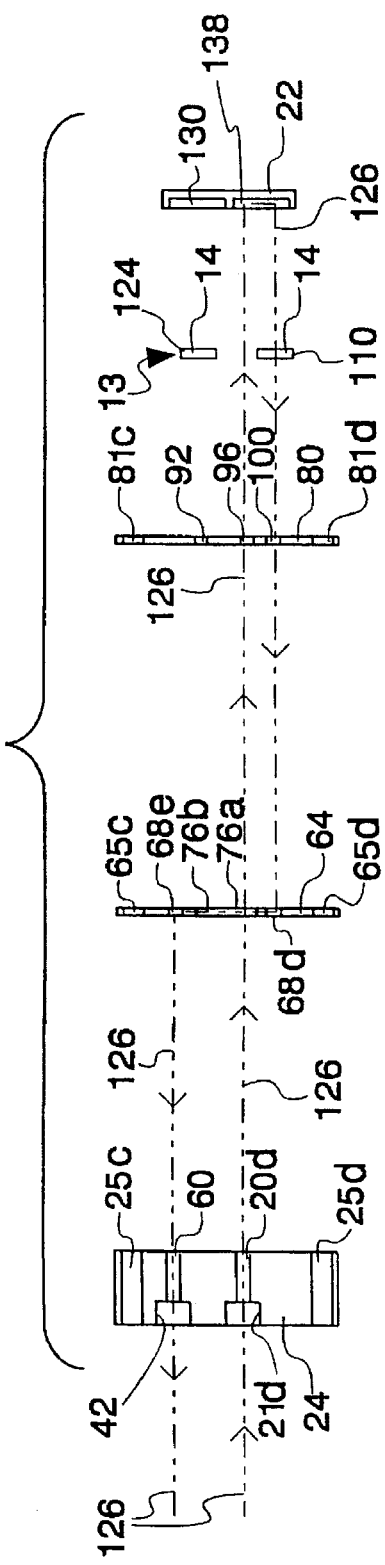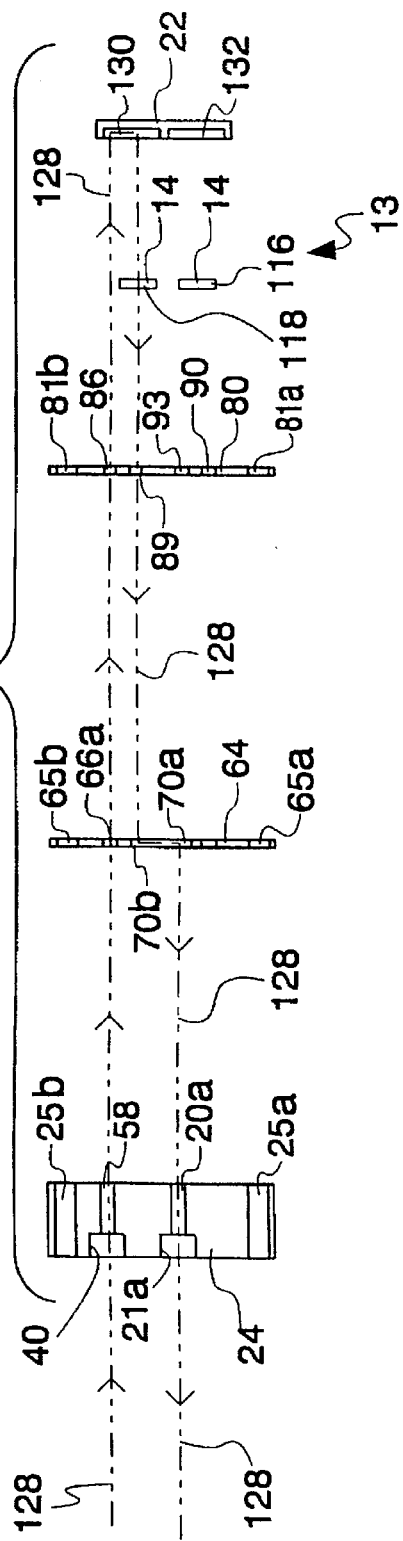

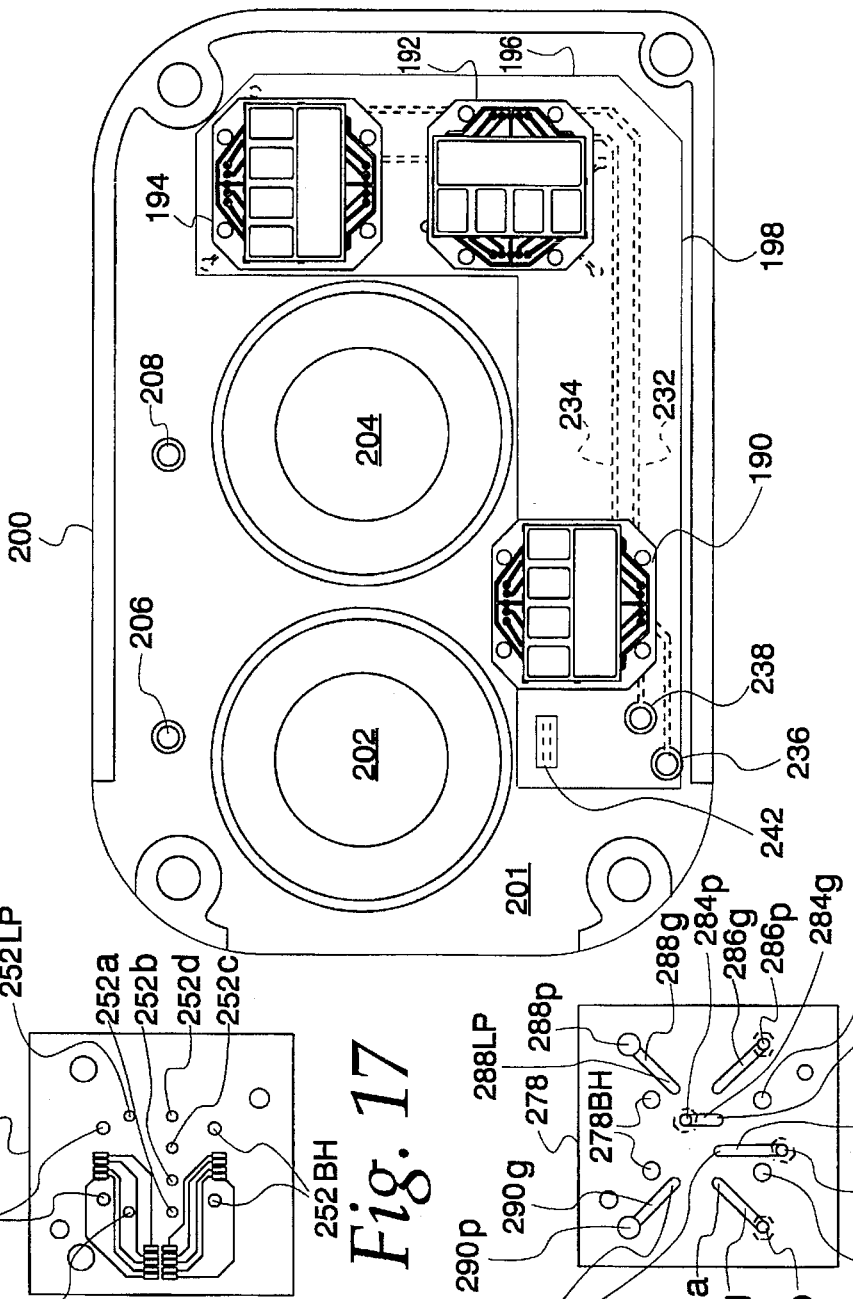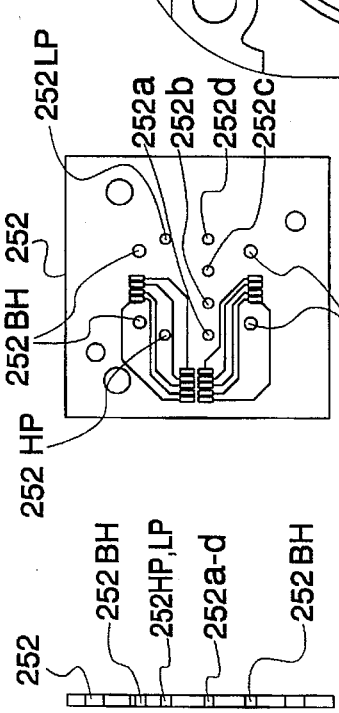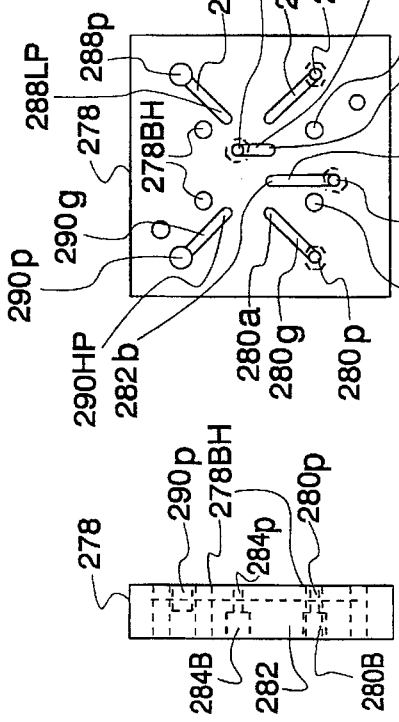

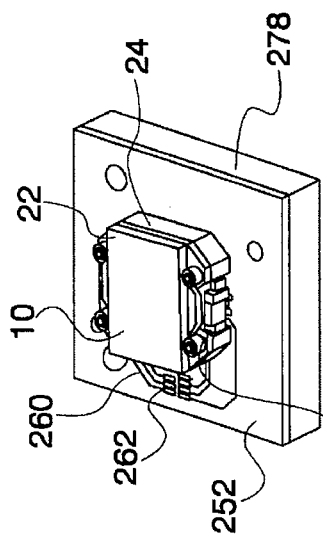
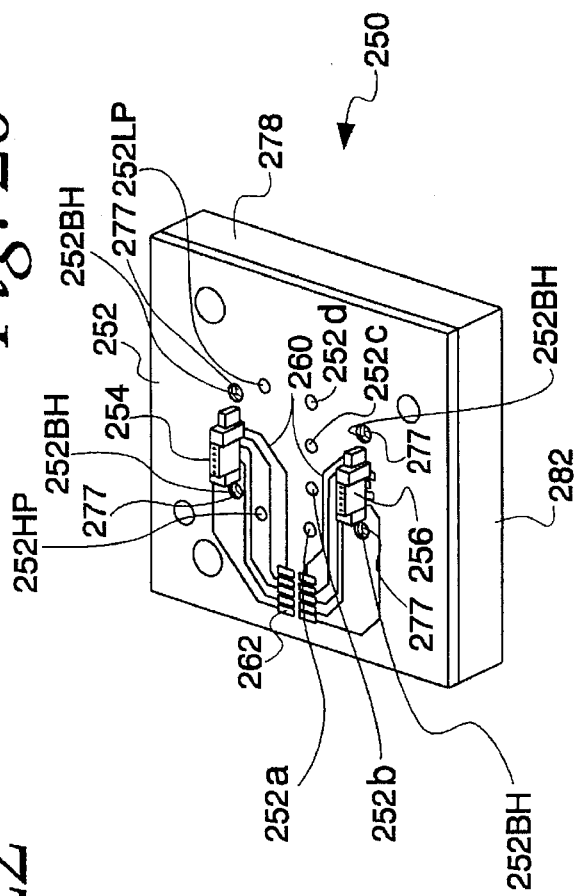
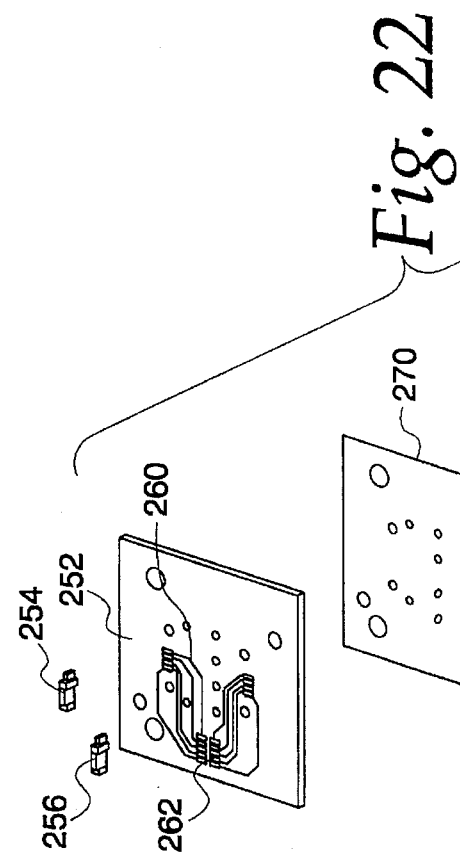
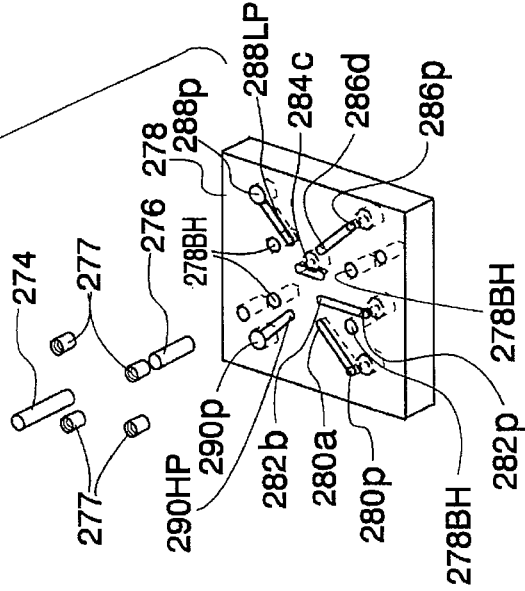

ELECTROFLUIDIC STANDARD MODULE AND CUSTOM CIRCUIT BOARD ASSEMBLY

BACKGROUND OF THE INVENTION

This invention relates to micromachined electrofluidic modules, their connection to a separate part or fixture, and their use in a multiplexing system.

Heretofore, there have been various and sundry assemblies of electronic and fluidic components. Such assemblies have, to one degree or another, attempted to obtain cooperation between the electronic and/or fluidic components in order to provide electrofluidic characteristics. Components have been assembled within a housing or in modular form. Such modular assemblies usually have an internal solenoid, electrical coil, electrothermal member, or an electrically responsive sensor such as used in a transducer, and have at least one fluidic passageway therein. Electrofluidic valves usually have both a fluidic inlet and a fluidic outlet, usually connected by fluidic hoses or pipes and have electrical leads attached thereto for connection to a control circuit. Solenoid controlled fluidic valves are usually quite large, although miniature solenoid valves are available, as will be described hereinafter. Also, as will be described hereinafter, there has been limited use of newer micromachined valves which are much smaller in size and use a movable member therein to modulate fluidic flow therethrough. While small micromachined valves are available, they are not effectively packaged to take advantage of their size where a large number of valves are needed, as in a complex fluidic system such as a fluidic multiplexing system.

Solenoid valves suffer a number of shortcomings when used in some applications where size, heat, weight, and noise of operation are important, such as in a dialysis system wherein over twenty solenoid valves have been used. Such dialysis systems are disclosed in U.S. Pat. No. 5,324,422, entitled "User Interface for Automated Peritoneal Dialysis Systems," issued to Colleran, et al., and assigned to Baxter International Inc.; and U.S. Pat. No. 5,350,357, entitled "Peritoneal Dialysis Systems Employing a Liquid Distribution and Pumping Cassette that Emulates Gravity Flow", issued to Kamen, et al., and assigned to Deka Products Limited Partnership. The pneumatic pressure distribution module in the Colleran/Kamen patents (see FIG. 9) has over 20 solenoid valves in two lines, with fluidic tubes extending between the inlet/outlets of the valves and the piston body.

While the pneumatic pressure distribution module disclosed in Colleran/Kamen serves its intended purpose of providing pneumatic actuating signals for the liquid valves, the module has several practical drawbacks. The module is relatively large and heavy, having an approximate size of twelve inches by four inches by two inches, and having a weight of approximately five pounds. The module includes over twenty solenoid actuated electromechanical valves, many of which are 3-way valves, requiring significant electricity and generating heat and substantial noise. The noise problems are particularly egregious, requiring a sound enclosure and remote mounting of the valves in a separate housing. The size of the Colleran module also resulted in mounting remotely from the piston element. The remote mounting causes a lag in the pneumatic actuating signals and liquid valve response time, and adding to the cost, size, and complexity of the overall system. A large number of lines and plumbing connections have to be made at the module and at the piston, which add to size, volume and complexity of the dialysis equipment. Thus, the shortcomings of the distribution module include the cost, size, weight, noise, heat, and power requirements. The shortcomings are accentuated by the fact that Colleran/Kamen systems are intended for home treatment of kidney dialysis patients, generally while the patient sleeps.

It was recognized that, while maintaining patient safety, it further would be desirable to reduce the size and cost of the pneumatic distribution module used with the peritoneal treatment apparatus. Unfortunately, components used in other applications often were found to be inadequate to meet these goals, particularly when used in peritoneal and other renal or medical treatment apparatus of the type discussed above.

In addition, the peritoneal treatment systems of the type shown in Colleran et al. may be relatively noisy due to the fact that the pneumatic valves are being actuated throughout the night while the patient is trying to sleep as he or she is connected to the peritoneal treatment system. Simple miniaturization of the valves, while continuing to use solenoidal valves, would not completely overcome the existing drawbacks as the relative volume of the manifolding with respect to the valves connected thereto would remain relatively large and, thus, the desired size and cost savings would not be achieved.

It was recognized that a distribution module might be made by trying to substitute for the larger solenoid valves, smaller miniaturized, solenoid valves of the type, for instance, available from SMC and identified by Model No. NVJ124A. Each of these three-way mini-valves is about an inch long, three-eighths (⅜) inch wide and three-quarters (¾) inch high. Very small tubular solenoid actuated valves are available from the Lee Company and identified by Serial No. LHDX0500700AA. Four to ten of the Lee three-way valves have been configured in manifolding systems on a plastic manifold block having a pair of primary inlets and a number of outlets equal to the number of valves. Unfortunately, however, very significant dimensional savings cannot be achieved with solenoidal valves due to the fact that solenoidal valves often draw a significant amount of electric current when actuated, generating waste heat which must be dissipated.

The prior art is replete with various and sundry electrofluidic circuits having electrical circuits, electromechanical valves, and fluidic manifolds. See, e.g., U.S. Pat. No. 4,095,863 to Hardin, entitled "Manifold Means and System for Electrical and/or Pneumatic Control Devices and Method"; U.S. Pat. No. 4,165,139 to Asbill III, entitled "Manifolding Means and System for Electrical and/or Pneumatic Control Devices and Method"; U.S. Pat. No. 3,547,139 to Van Berkum, entitled "Fluid Logic Pack"; U.S. Pat. No. 3,646,963 to Klee, entitled "Duct System for Fluid Pressure Medium Operated Regulating, Control and Measuring Apparatus"; and U.S. Pat. No. 4,549,248 to Stoll, entitled "Electrofluidic Circuit Board Assembly with Fluid Ducts and Electrical Connections". Each of the aforementioned references suffers certain drawbacks in their large size, heavy weight, and application-specific designs.

In recent years, it has become known in the art that micromachined valves, for instance, of the type disclosed in U.S. Pat. No. 5,069,419 to Jerman, are available commercially. Such valves have each been enclosed in individual packages with a single inlet and a single outlet for control of small amounts of fluid flow therethrough. The silicon micromachined valves are quite small, being embodied on square or rectangular silicon dies which may be measured into fractions of an inch and are only a few thousandths thick. However, the housings within which the micromachined valves have been enclosed are orders of magnitude larger than the valves themselves and are relatively bulky in comparison to the micromachined valve itself. In addition, micromachined valves are relatively fragile as compared to solenoidal valves. However, they do not draw large amounts of current as they are usually activated by the heating caused by electric current flowing through a doped region, causing differential expansion of layers in the micromachined valve effecting movement between a boss and a valve seat. Such valves are available, for instance, from IC Sensors Model No. ICS 4425. Similar valves are available from Redwood Systems and are sold under the trademark "FLUISTOR™". The valves are packaged one per package with the valves specifically being mounted within a TO8 can having a single gas inlet and a single gas outlet. The TO8 can may be mounted projecting upwardly from a printed circuit board on which electrical traces may be formed to provide an electrical connection to the valve so that electrical signals may be fed to the valve to control its state, and thereby to control fluid flow through the valve.

Similarly, the shape memory alloy film actuated microvalve disclosed in Johnson U.S. Pat. No. 5,325,880, discloses the packaging of a microvalve in a TO8 can, see FIG. 2. U.S. Pat. No. 5,329,965 to Gordon, entitled "Hybrid Valving System for Varying Fluid Flow Rate", discloses a schematic diagram of a fluid flow valving system incorporating a Fluistor™ microvalve and disclosing as an alternative, a gas microvalve Model No. 4425 sold by IC Sensors. The Gordon '965 patent apparently requires the use of a separate inlet tube and outlet tube as well as a circuit board.

In addition to Jerman, Pat. No. 5,069,419, other micromachined devices are disclosed in U.S. Pat. No. 5,325,880 to Johnson, et al., entitled "Shape Memory Alloy Film Actuated Microvalve"; U.S. Pat. No. 5,180,623 to Ohnstein, entitled "Electronic Microvalve Apparatus and Fabrication"; U.S. Pat. No. 4,821,997 to Zdeblick, entitled "Integrated, Microminiature Electric-to-Fluidic Valve and Pressure/Flow Regulator"; and U.S. Pat. No. 5,322,258 to Bosch, et al., entitled "Micromechanical Actuator."

It is to be understood that the term micromachined devices as used herein is generic not only to micromachined electrofluidic valves but also to other micromachined devices such as electrofluidic pressure transducers. An example of a commercially available micromachined pressure transducer is Model Number FPM-15PG, available from Fujikura of Japan. The pressure transducer body has a single fluidic input line for a single transducer therein, as well as electrical connections for the single transducer for plugging into appropriate electrical devices. The aforementioned Fujikura pressure transducer has been used commercially with the pressure distribution module disclosed in the Colleran '422 patent, see reference numeral 178, FIG. 18.

Two other patents, the Bosch '258 patent and the Zdeblick '997 patent, disclose arrays of microvalves, see Bosch, FIG. 6, and Zdeblick, FIG. 66. However, neither Bosch nor Zdeblick disclose the electrical circuitry and fluidic connections needed for handling the fluidic inputs and outputs for the valves in the arrays.

The use of electrostatically actuated microvalves, which may use a shape memory film relying on the martensitic transformation phenomenon, in a matrix-like arrangement is disclosed in U.S. Pat. No. 5,284,179 to Shikida, et al., entitled "Valve and Semiconductor Fabricating Equipment Using the Same". The Shikida '179 patent discloses multiple inlets and multiple outlets, with multiple shape memory microvalves which may be placed in a single layer within a fluidic manifold or may be placed at multiple levels within a more complex fluidic manifold, see FIGS. 7b, 8, and 18. The Shikida patent suffers from drawbacks in that it appears to be a complicated and difficult system to build, and the microvalves are difficult or impossible to access for repair or replacement. Moreover, the Shikida disclosure is for an application-specific design, and is not a package or module of electrical and fluidic components having general applicability. That is, unlike individual valves which may be attached or detached if one of them becomes defective, the entire matrix must be discarded if one valve becomes defective. Further, the microvalves do not have standard fluidic and electrical connectors as do solenoid valves, allowing the rearrangement of the valves for different functions.

As stated above, while the microvalve inside the TO8 can of ICS 4425 or the Fluistor™ valve is very small, the package is quite large and each package requires separate fluidic connections and electrical connections. It can be seen that in order to provide a plurality of valves, as in the Colleran '422 patent, would require a large number of fluidic lines and a large number of electrical connections, resulting in a very complex and confusing array of discrete elements, including valves, fluidic lines and connectors, and electrical lines and connectors.

What is needed is an electrofluidic module, specifically a highly miniaturized electrofluidic module which can perform the function of a multiplexing system able to selectively connect one or more of a plurality of fluidic inlets to one or more of a plurality of fluidic outlets, but which occupies a very small volume, uses very little electrical current to control and thus produces little waste heat and which is reliable and may be manufactured inexpensively. Preferably, such a module should permit easy installation and replacement and should be provided with a standard fluidic interface and a standard electronic interface.

SUMMARY OF THE INVENTION

In accordance with the present invention there has been developed a highly miniaturized electrofluidic system such as for a multiplexing task that occupies a very small volume and preferably uses very small micromachined electrofluidic devices such as electrofluidic valves. This is achieved in part by providing a plurality of micromachined electrofluidic devices in a single small, flat module rather than supplying the same number of individually packaged devices separately. Also, the weight of these plural micromachined devices is considerably lighter because of their combination in a single small, flat, layered package. Furthermore, the cost of the electrofluidic system is considerably reduced because the multiple valve modules can be made from standard circuit board material (FR-4) using traditional, inexpensive multilayer circuit board fabrication techniques. Packaging multiple micromachined devices in a common single miniaturized layer package, without numerous individual air lines and related connections, yields substantial size, weight and cost savings. Advantages in assembly and serviceability occur because the standard layered module may be provided with standard predetermined fluidic inlets and outlets and a standard electrical connector for connection to a mounting electrofluidic element such as an electrofluidic board having fluidic passageways and a mating electrical connector. The electrical connector on the standard layered module may be fastened to a mating electrical connector through the use of any suitable connecting means, for example, a standard mating interconnect pin-and-socket assembly requiring minimal insertion force. This makes the module ideal for quick assembly or for replacement with respect to the electrofluidic element in the event of a valve failure in the module. This overcomes the shortcomings of prior art microvalves which often have pigtail electrical wire leads that need to be individually soldered which is time consuming and may damage the silicon material if a heat sink is not used when soldering.

Additionally, the volume occupied by the standard module is reduced by providing a return flow means on the module for redirecting the incoming fluid flow in a reverse return direction so that both fluidic inlets and outlets may be in a common face of the standard module for flush mounting against a face of an electrofluidic member such as an electrofluidic circuit board. That is, rather than having large and separate inlet pipes or hoses connected to opposite sides of each of the multiple micromachined valves, a common return manifold is disposed, to return the fluid flow to the inlet/outlet face of the module. Thus, the height and volume of the standard module is reduced by elimination of a series of linear extended connections.

Preferably, the flush mountable face of the standard module is mounted flush against the electrofluidic member or circuit board which has fluidic passageways in its surface so that no fluidic pipes or hoses are extended between the board and the module.

Likewise, in accordance with another aspect of the invention, it is preferred that an electrofluidic member or circuit board be mounted flush against a separate fixture and that the fixture have fluidic passageways therein so that fluid may flow directly from the fixture through openings and fluidic passageways in the board to and from the standard modules without the use of pipes or hoses between the board and the fixture. By way of example, the piston body of the dialysis apparatus is provided with fluidic passageways therein and the electrofluidic member or circuit board is mounted against the piston body with openings in the board receiving and returning fluid with respect to the piston fluidic passageways without the use of any fluidic pipes or hoses. The standard module is likewise flush mounted with its fluidic inlets and outlets on its manifold layer face being connected to the fluidic passageways in the board. Because of a return manifold layer on the module on the side of a layer of micromachined devices in the module, returns fluid to manifold layer, both inlet and outlet fluid flows are through the same manifold layer and face.

The quality of the electrofluidic standard module is improved over that of a conventional fluidic circuit with similar functionality. This is because reduction in the number of parts translates directly into improved quality. Advantages in quality control also accrue to the invention because the standardized electronic and fluidic interconnections allow for easy quality control testing of the module after assembly. The module of the invention further provides for a uniform connective standard, thereby establishing standardized electronic and fluidic interconnections and the straightforward adaptation of the module into a wide variety of applications.

The functionality of the electrofluidic standard module and custom circuit board assembly is quite diverse and capable of accommodating electronic and fluidic components to perform a variety of functions. These components may include any desired combination of two-way valves, three-way valves, pressure/flow/temperature sensors, pressure/flow regulators, programmable fluidic components, combination fluidic circuits, transistors, micromachined pumps, amplifiers, and other electronic and/or fluidic components. The aforementioned components and functions are by way of example, and are not intended to limit the choices which are or may become available in the art.

The preferred electrofluidic module is comprised of flat layers including a layer having at least one micromachined device, for example, a plurality of micromachined valves that are disposed adjacent one another and which are electrically connected to circuits on an adjacent electrical layer which operates the valve members. The module also has a manifold layer with fluidic passageways and fluidic inlets and outlets therein on one face of the module, and the fluidic passageways in the manifold layer are in fluid communication with the fluidic passageways in the micromachined valves. Preferably, the electrical layer comprises an electrical circuit board with electrical traces thereon defining electrical circuits for operating each of micromachined valves. These electrical circuits are electrically connected to an electrical connector for mechanical and electrical connection with a mating electrical connector on the electrofluidic board element without the use of soldering techniques.

From the foregoing, it will be seen that there is provided a new and improved method of making and/or packaging a plurality of miniature or micromachined fluidic and electronic components in a very miniaturized, inexpensive flat-pack module. The methods disclosed in this invention allows such a flat-pack module to be flush mounted for fluidic connections into a larger fluidic system and to be connected through matable electric connectors to an electrical controller for operating the micro devices in the flat-pack module. Thus, a flat-pack module having a plurality of microvalves may be incorporated into a larger electrofluidic system having additional fluidic components as part of a separate fixture. The fluids may be gases, such as air under pressure or vacuum, or liquids. The microvalves are proportional and can be used to adjust flow rates as well as to open and close the flow paths.

From the foregoing, it will be seen that the module has fluidic conduits and electronic circuits, with a base supporting fluidic and electronic components, as well as fluidic interface connections for communicating fluids between the base and a separate fixture, electronic interface connections for communicating electrical signals and/or power between the base and the separate fixture, and a mechanical interface connection for securing the base to the separate fixture. The preferred module also may include a return manifold cap layer for protecting the fluidic and electronic components and for returning the fluids to the base and to the micromachined electrical devices.

Also, it will be seen that the present invention of an electrofluidic module overcomes the prior art drawbacks, including the large size, weight, heat, noise, inefficiency, and lack of general applicability of prior art electrofluidic systems making use of conventional components.

In many instances, the electrofluidic member or circuit board may have several detachable modules mounted on it and the board may have an additional connector for connection to a ribbon cable leading to an electrical controller for operating the sequence of microfluidic valves to do the required multiplexing. Alternatively, a controller may be mounted directly on the electrofluidic member for communication through circuits provided for that purpose. In other instances, a single module may be attached to a dedicated electrofluidic member to form an assembly that can be used with various fixtures.

In accordance with another embodiment of the invention, a fixture is provided with fluidic passageways and an electrofluidic member such as an electrofluidic circuit board is attached to the fixture with fluidic inlets and outlets in the board in fluid communication with fluid in the fixture. At least one micromachined device is affixed to the board and fluidic passageways in the device are in fluid communication with the fluidic inlets and outlets in the board and thereby with the fluidic passageways in the piston. An electrical connector on the circuit board is attached to an electrical connector on the micromachined device.

A further embodiment of the invention involves the use of the electrofluidic module for control of multiple liquid valves, in that the standard module may be incorporated into a piston element whereby the outputs of the standard module may be directed through a custom electrofluidic member or circuit board and distributed into a predetermined number and configuration of pneumatic actuators for liquid valves. One specific application for the invention is in an automated peritoneal dialysis system such as disclosed in the Colleran '422 patent, wherein the large separate fluidic control distributor with over twenty solenoid valves and 14 fluidic tubes to and from the piston body has been replaced, for the most part, by a small printed circuit board mounted on the piston body and having a few standard modules each with multiple micromachined electrofluidic valves therein. The proximity of the control modules to the pneumatic actuators eliminates lengthy sections of tubing, thereby decreasing lag time in the system previously caused by the required time to achieve the desired pressure and flow rate in the tubing sections. Accordingly, the invention provides faster response time and improved manufacturability, assembly, and serviceability, while decreasing the size, weight, noise, heat, power requirements, and cost of the system.

BRIEF DESCRIPTION OF THE DRAWINGS

FIG. 4 is a plan view of a base layer of the electrofluidic module shown in FIG. 1;

FIG. 5 is a plan view of a first intermediate layer of the electrofluidic module shown in FIG. 1;

FIG. 6 is a plan view of a circuit layer with a superimposed device layer including a plurality of microvalves positioned on the circuit layer, which components are incorporated into the electrofluidic module shown in FIG. 1;

FIG. 7 is a plan view of a fluidic return cap for positioning over the device layer and the circuit layer;

FIG. 8 is a plan view of the electrofluidic module shown in FIG. 1;

FIG. 9 is a cross-section taken along lines 9—9 of FIG. 8, having the portions exploded to show details of a first fluid flow path through the module;

FIG. 10 is a cross-section taken along lines 10—10 of FIG. 8, having the portions exploded to show details of a second fluid flow path through the module;

FIG. 15 is a further rear elevational view of the piston body and the base plate of FIG. 14, with three electrofluidic modules in place;

FIG. 16 is a side elevational view of a printed circuit board for use in an electrofluidic module mounting fixture;

FIG. 17 is a plan view of the printed circuit shown in FIG. 16 showing details of a plurality of traces thereon;

FIG. 18 is a side elevational view of a base layer for supporting the printed circuit board shown in FIGS. 16 and 17;

FIG. 19 is a plan view of the base layer shown in FIG. 18 showing details of a plurality of fluidic passageways therein;

FIG. 20 is a perspective view of the electrofluidic module shown in FIG. 1 mounted upon the fixture;

FIG. 21 is a perspective view of the fixture shown in FIG. 20;

FIG. 22 is an exploded perspective view of the fixture shown in FIG. 21;

DETAILED DESCRIPTION OF THE PREFERRED EMBODIMENTS

Figure 1:
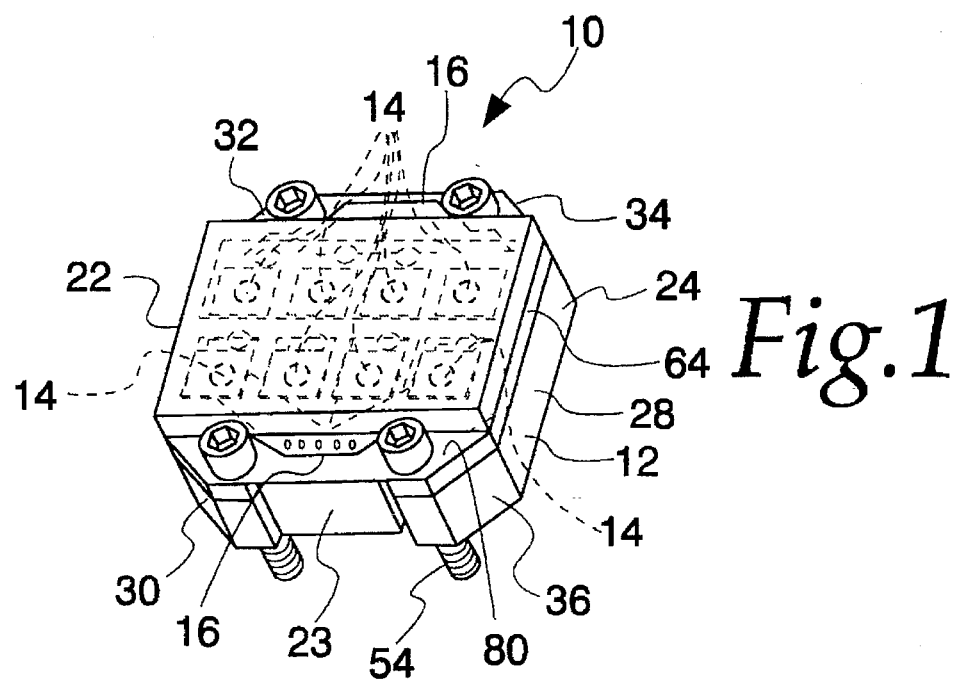
FIG. 1 is a perspective view of an electrofluidic module embodying the present invention.
Figure 2:
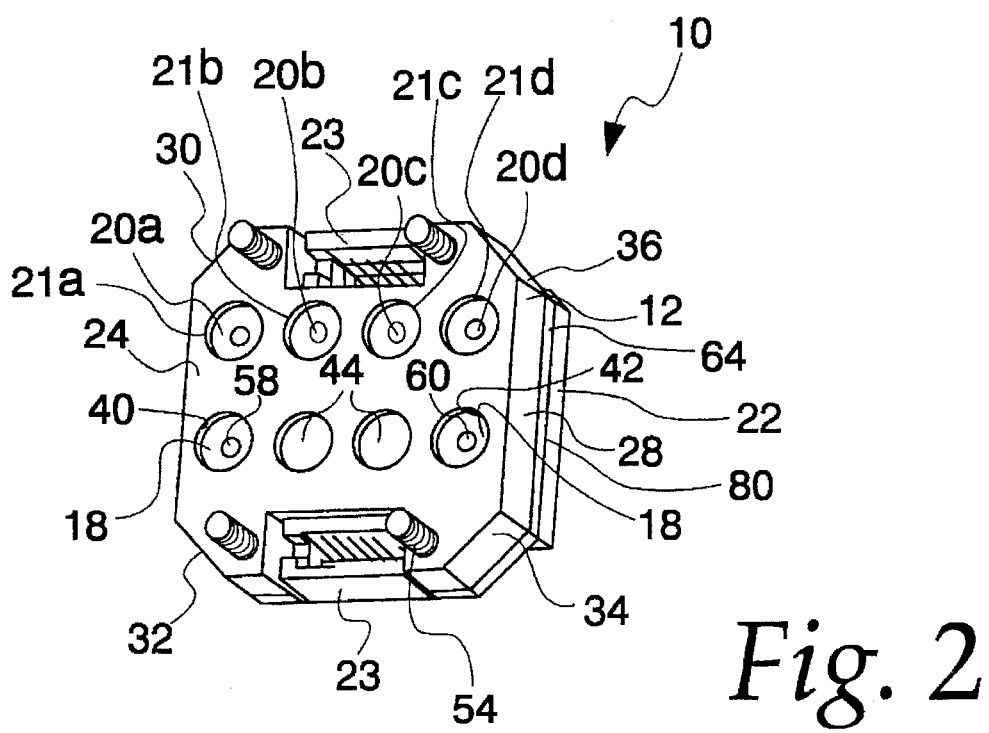
FIG. 2 is a perspective view of the electrofluidic module shown in FIG. 1, showing details of the bottom thereof.
Figure 3:
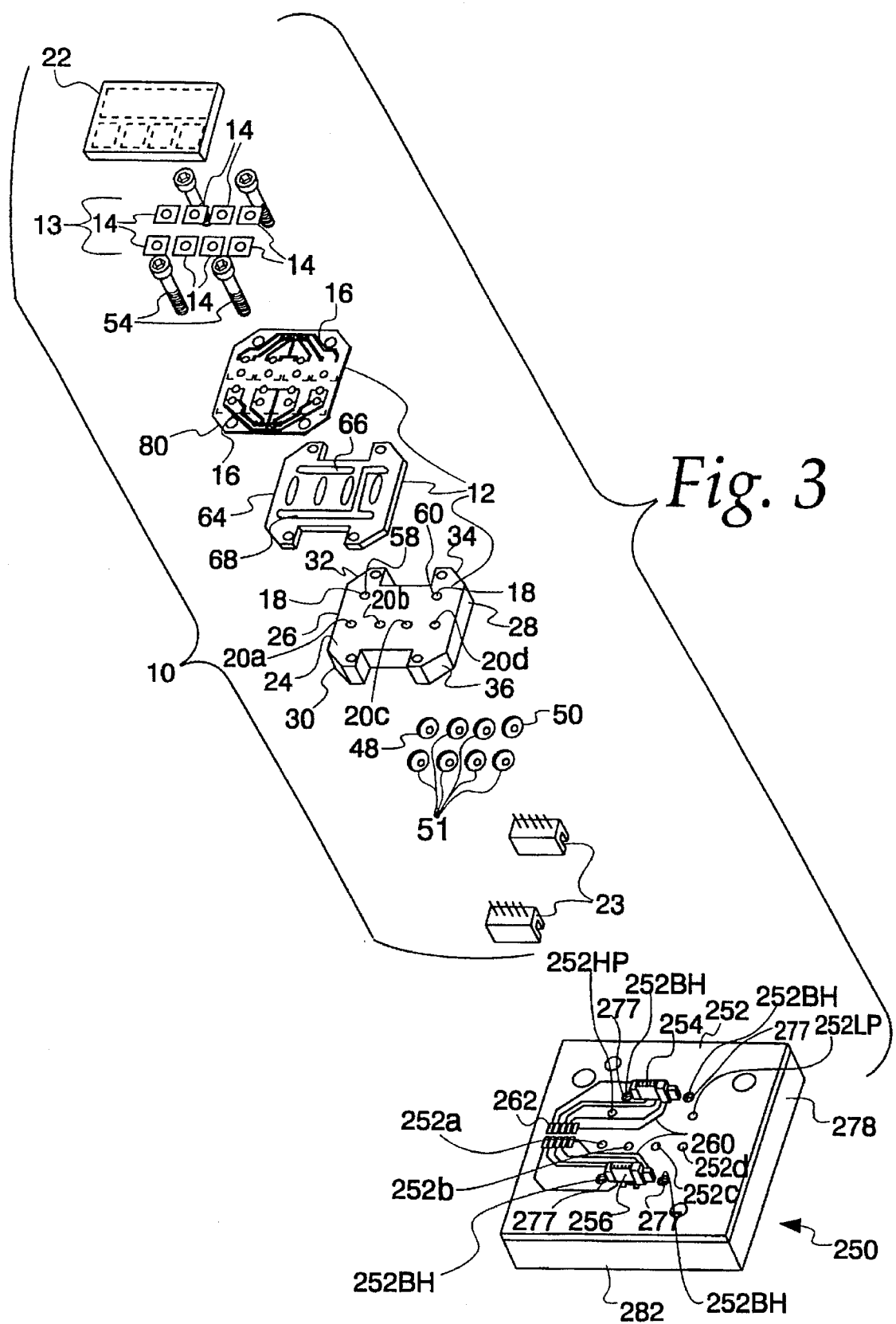
FIG. 3 is an exploded, perspective view of components of the electrofluidic module shown in FIG. 1 and further showing an underlying separate fixture, the combination of the module and the fixture comprising an electrofluidic assembly.

Referring now to the drawings and especially FIGS. 1 through 3, a miniature electrofluidic module embodying the present invention is generally shown therein and identified by numeral 10. As shown in FIGS. 3 and 20, the electrofluidic module 10 may be mounted on a separate electrofluidic fixture 250, for fluidic and electronic communication between the module and the fixture.

The miniature electrofluidic module 10 may be constructed around a base unit or electrofluidic member 12, which may comprise three layers 24, 64, 80, as discussed in more detail below. The electrofluidic member 12 supports a preferably substantially flat or planar device layer 13, including a plurality of micromachined devices 14. A plurality of electrical circuits 16 is formed on the electrofluidic member 12, and the circuits are connected to the micromachined devices 14 to operate them in order to modulate fluid flow from a plurality of inlets or outlets 18 through the micromachined devices 14 and through a plurality of bidirectional ports 20, each of which may be selected to serve as an inlet or an outlet depending on the fluid distribution manifold paths, the state of the respective microactuators 14, and the positive or negative relative pressure at each port 20 with respect to the pressure at the associated inlet or outlet 18. A return fluid flow director or manifold cap 22 completes a fluid flow path between the fluidic inlets or outlets 18 and the fluidic inlets/outlets 20. Manifold cap 22 may be mounted above device layer 13 and be supported by the top electrofluidic member layer 80 and, thus, by the electrofluidic member 12. A pair of electrical connectors 23, which may each have five pins, provides an electrical coupling between the electrical circuits 16 and the environment in which the miniature electrofluidic module 10 operates.

The module 10 and the fixture 250 may be made from circuit board material such as FR-4 or from ceramic substrates such as aluminia or other ceramic materials, or from other suitable materials. The material may be selected with due consideration for its properties, such as convenience of fabrication (in the case of FR-4), inherent cleanliness and chemical resistance (in the case of aluminia and other common ceramic materials), and other properties such as insulating characteristics, light weight, machining capabilities, strength, cost-effectiveness, and such other factors as may be relevant for specific applications.

The electrofluidic member 12 comprises a substantially rectangular parallelepiped base layer 24 having a pair of rectangular side walls 26 and 28 and four chamfered corners 30, 32, 34 and 36. The inlets or outlets 18 may comprise pressure inlet 58 and a subatmospheric exhaust or vacuum outlet 60. Pressure inlet passage 58 may be provided with a blind pressure inlet bore 40, while vacuum outlet passage 60 may be provided with a blind vacuum outlet bore 42. These passages serve to communicate pressurized or rarefied air, at a pressure above or below atmospheric pressure, but usually in the range of ±1.5 to 10 psig, preferably about ±5 psig. The electrofluidic module 10 may be used to transmit pneumatic signals to actuate liquid valves, e.g., in medical devices such as automated peritoneal dialysis treatment systems. A pair of inlet or outlet O-rings 48 and 50 are seated, respectively, within the bores 40 and 42. The inlet or outlet O-rings 48 and 50 provide sealing between whatever pneumatic supply device is connected in fluid communication with the inlet 58 and the outlet 60. The inlet channel 58 and outlet channel 60, respectively, couple either a source of pressurized air or a source of below-atmospheric pressure air through other layers to the micromachined valves 14.

An intermediate manifold layer 64 is positioned above the base layer 24 with passageways in fluid communication with inlets or outlets 18 and inlet/outlets 20. More specifically, the intermediate manifold layer 64 provides generalized routing between the microvalves 14 and the inlets or outlets 18 and inlet/outlets 20. The intermediate manifold 64 is substantially flat and planar and has a plurality of slots formed therein. Included in the slots are an elongated pressure inlet slot 66, a substantially h-shaped vacuum outlet slot 68, and four inlet/outlet slots 70, 72, 74, and 76, see FIGS. 3, 5.

Figure 11:
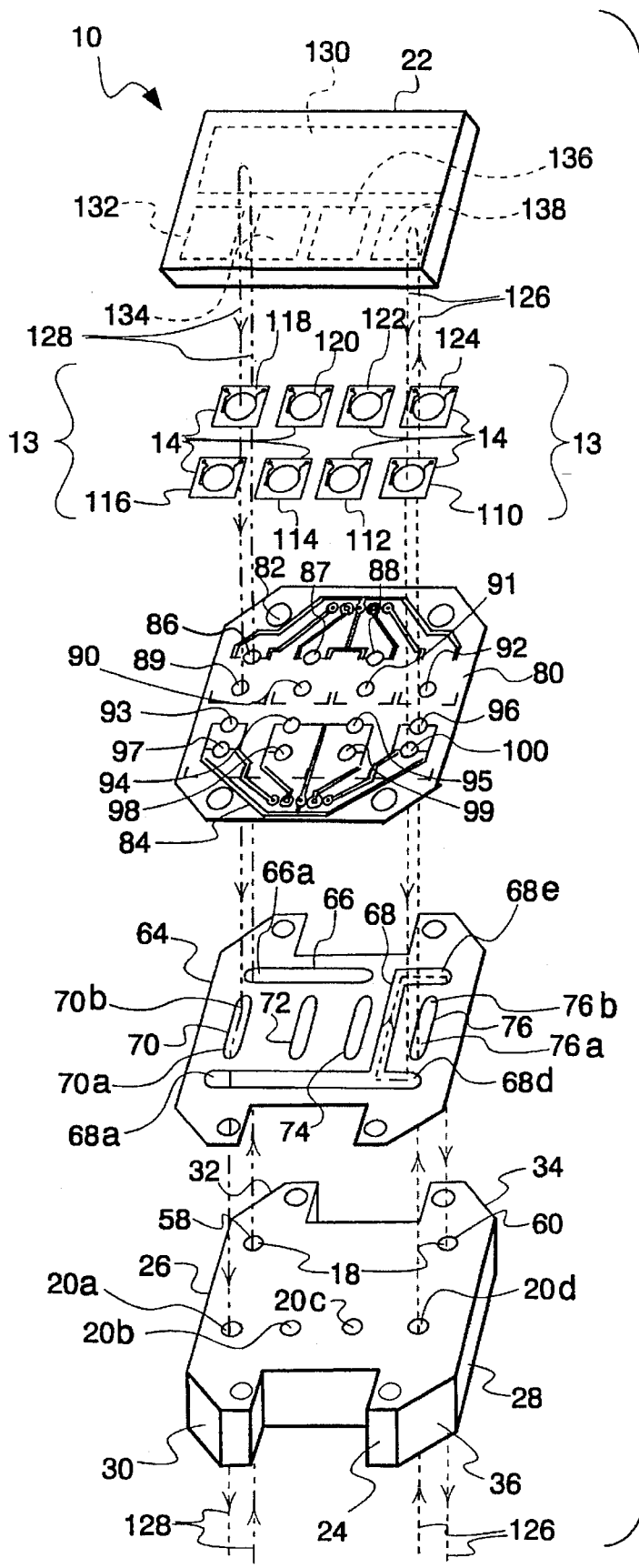
FIG. 11 is an exploded perspective of the electrofluidic module shown in FIG. 1 shown in part schematically to illustrate two simultaneous flow paths through respective portions of the module.

A printed circuit board 80 is positioned above the intermediate manifold layer 64 and has a plurality of electrical traces or conductive paths 16, which may include two sections 82 and 84 formed thereon by any conventional method of forming electrical traces on a printed circuit board, see FIGS. 6, 11.

Base layer 24 also is provided with four inlets or outlets 20, which will be identified with reference numerals 20a–d. As shown in FIGS. 2 and 3, inlets/outlets 20a–d are provided with blind bores 21a–d respectively, for receiving O-rings 51, which provide sealing for external connections or channels used to transmit fluids, e.g., for pneumatic actuating signals.

The O-rings 51 effectively extend flow passageways 20a–d through the entire thickness of base layer 24. If desired, the internal diameter of the O-rings may be substantially equal to the internal diameter of passageways 20a–d and the internal diameter of mating passageways 252a–d in a separate fixture upon which module 10 may be mounted, FIG. 3, see also FIG. 14. In this way, each fluid flow path between the module passageways and the fixture passageways may be substantially straight, smooth, unobstructed, and characterized by a relatively uniform cross-section or diameter.

The layers 24, 64, 80 of electrofluidic member 12 may be adhered to one another by a suitable adhesive compound or adhesive gaskets (not shown), to provide desirable fluid-tight, air-tight, and vacuum-tight characteristics. The micromachined devices 14 may be surface-mounted onto printed circuit board 80. The return manifold cap 22 may be mounted onto printed circuit board 80 by any suitable adhesive or fasteners, again, preferably air-tight and vacuum-tight around the cap/circuit board interface.

The member 12 and, thus, the module 10, may be secured to a separate fixture 200, 250 (FIGS. 3, 14) through the use of any suitable fasteners, such as threaded bolts 54, or a snap-fit connection, or the like. The bolts 54 may be inserted through bolt holes 81a–d in printed circuit board 80, bolt holes 65a–d in intermediate manifold layer 64, and bolt holes 25a–d in base layer 24, see FIGS. 4–6. The threads on bolts 54 mate with threaded inserts 277 in fixture 250, FIG. 3, or in threaded bolt holes BH in fixture 200, FIG.

Valve passageways 86–100 communicate generally between the slots formed in the intermediate manifold layer 64 and the plurality of valves 14, FIG. 11. The valves preferably are in a generally flat planar layer 13. The plurality of valves 14 includes valves 110, 112, 114, 116, 118, 120, 122, and 124. The valves form paired combinations 116 and 118, 114 and 120, 112 and 122, and 110 and 124, each of the valve pairs being associated via the respective inlet/outlet slots 70, 72, 74, and 76 with inlet/outlet ports 20a, 20b, 20c, and 20d. The cap or return manifold 22 is positioned above the valves and has formed therein an elongated rectangular pressure manifold section 130 and a plurality of individualized vacuum manifold sections 132, 134, 136, and 138. Preferably, the cap 22 is made of clear polycarbonate or another suitable clear material to permit visual inspection of the microvalves and, in some cases, the fluids.

As may best be seen in FIG. 11, examples are shown of a typical pressurized air flow path 128 and a typical subatmospheric air flow path 126. See also FIGS. 9 and 10.

Describing first the vacuum communication within the module 10, a vacuum source is coupled to air outlet or exhaust port 60 to draw a vacuum. The vacuum is communicated upstream from the vacuum source to the passageways and components as described hereafter. Beginning at the vacuum source which is introduced to exhaust port 60, the vacuum is communicated to the vacuum slot 68 in intermediate manifold layer 64, and then to the overlying vacuum passageways 97–100 in circuit board 80. The vacuum passageways 97, 98, 99, 100 communicate vacuum to the overlying vacuum-side valves 116, 114, 112, 110, respectively, which places a reduced pressure on the undersides of those valves (FIG. 11).

If typical vacuum-side valve 110 is caused to be opened by providing a suitable electrical signal on the traces 84, vacuum is communicated from valve 110 to vacuum manifold chamber 138, from thence to aperture 96, to the inlet/outlet slot 76 comprising a passageway, and ultimately to the inlet/outlet opening 20d.

It will be appreciated that in the aforementioned example, the air flow will be from the relatively higher pressure inlet/outlet port 20d, proceeding along the typical vacuum side air path 126 to vacuum exhaust port 60, where air at subatmospheric pressure will be exhausted to the vacuum source. Referring still to FIG. 11 and also to FIG. 9, a typical vacuum-side air flow path 126 is shown, with the arrowheads designating the direction of air flow. Upon opening typical vacuum-side valve 110, air is drawn into the inlet/outlet passageway 20d, upwardly through inlet/outlet slot 76, upwardly through aperture 96, upwardly through vacuum manifold section 138, and then downwardly through valve 110, aperture 100, L-shaped vacuum outlet slot 68, and ultimately outwardly through vacuum exhaust passageway 60, FIGS. 9 and 11.

It may be appreciated that the manner in which the module 10 is plumbed causes the vacuum valves 110–116 to have lower pressure presented at the undersides of the valves rather than on top, thereby biasing valves 110–116 closed. This is because the valves 110, 112, 114, 116 overlie vacuum apertures 100, 99, 98, 97, respectively, and the apertures communicate with vacuum slot 68, upon which a vacuum is drawn through exhaust port 60. Likewise, the pressure maintained in manifold section 130 biases valves 118–124 closed.

As shown in FIGS. 10 and 11, a typical pressurized air stream 128 may be supplied through the pressure inlet 58, upwardly through the pressure inlet slot 66, and thence upwardly through pressure distribution apertures 86, 87, and 88, into the pressure header 130, and thence downwardly to the tops of pressure-side valves 118–124. If electrical energy is supplied to the valve 118 through the leads 82 (FIGS. 6, 11), the valve 118 opens, connecting a positive pressure flow path downwardly through aperture 89 to the inlet/outlet slot 70, providing an outlet pressure stream 128 through outlet 20a (FIGS. 10, 11).

Generally, for a given inlet/outlet selected from the inlet/outlets 20, it will be desirable to activate only one of the two microvalves 14 associated with that inlet/outlet. Thus, in one of the above examples, the decision to open vacuum-side microvalve 110 will result in the flow of subatmospheric air stream 126 into port 20d. In that instance, pressure-side microvalve 124 (paired with microvalve 110) will remain closed, so as to avoid counteracting the subatmospheric air flow.

It will be observed, however, that if desired, the electrofluidic module 10 of the invention may be used to mix two or more streams, such as two gases or two liquids of different composition, or to add or subtract actuating signals such as air pressures. The mixing or addition, if desired, may be accomplished by opening both of two paired microvalves, e.g., 110 and 124. In the embodiment illustrated, the effect of opening both microvalves 110, 124 would be to add the positive gauge pressure at inlet 58 to the negative gauge pressure at exhaust 60, the sum being approximately the expected pressure at the inlet/outlet 20d associated with the paired valves.

In this respect, the module 10 may be used to provide fluidic logic capabilities. Other uses of the invention for fluidic logic purposes will be apparent to those skilled in the art.

Figure 12:
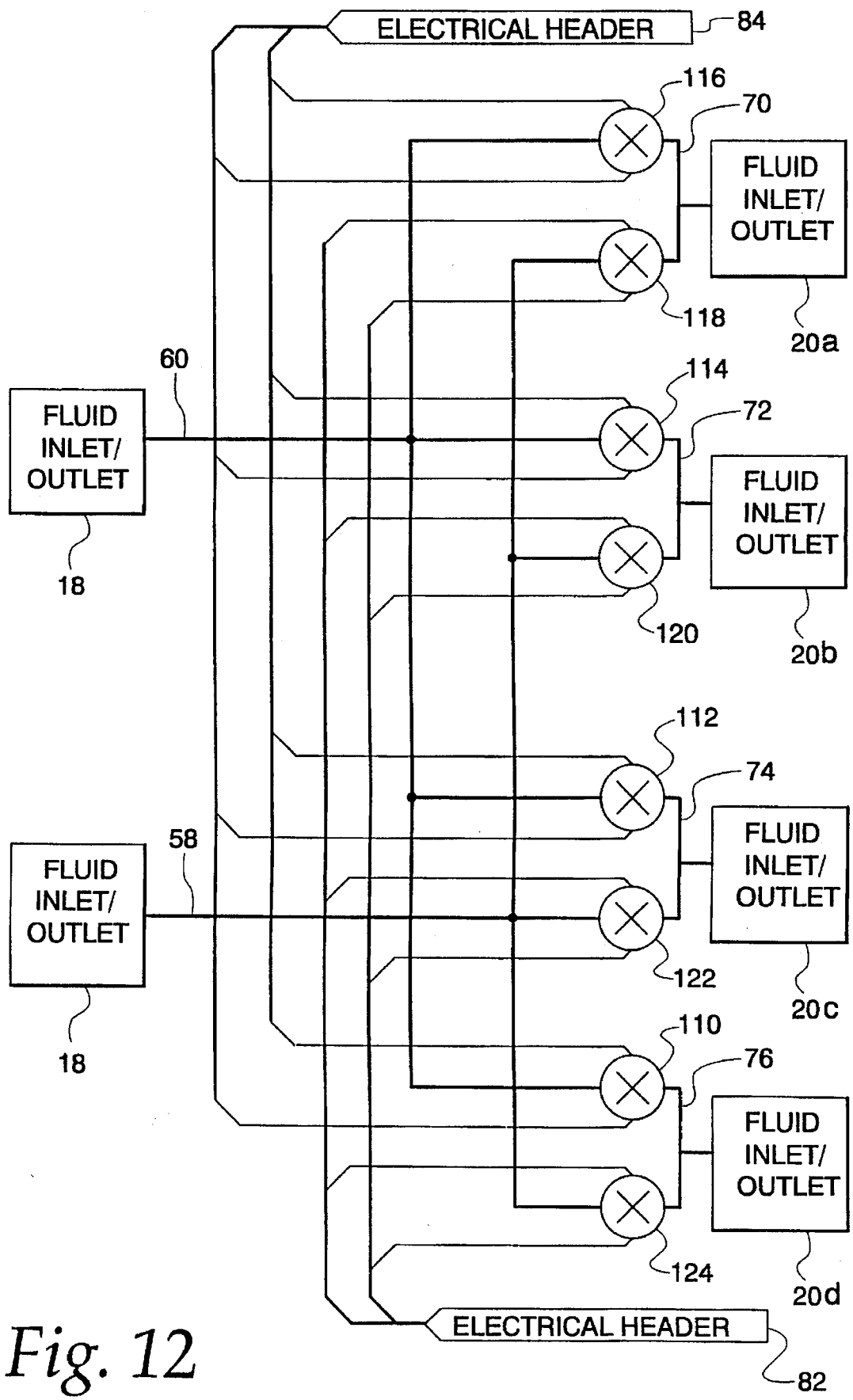
FIG. 12 is a schematic diagram of the electrofluidic module shown in FIG. 1 illustrating the connections to a pair of electrical headers and a pair of fluid sources.

In FIG. 12, a schematic drawing of the electrical circuitry and the fluid flow paths within module 10 is provided. It may be observed that the eight two-way valves 14 of module 10 are configured to perform the equivalent function of four three-way selector valves. For each inlet/outlet 20, a pair of valves associated therewith permits either of two fluid streams (e.g., pressurized air or rarefied air) to pass through the inlet/outlet 20.

Similarly, there are any number of flow configurations available for an electrofluidic module in accordance with the invention. The base layer 24 may be provided with any desired number and configuration of inlets or outlets. The intermediate manifold layer 64 may be provided with any desired number and configuration of channels or slots. The circuit board layer 80, device layer 13, and return manifold cap 22 provide similar flexibility in their design and operation.

Thus, it will be observed that the electrofluidic interfaces or connections provided by the invention can be standardized to any number of predetermined standards. One of these standard interfaces is that disclosed for the preferred embodiment 10. An analogy can be drawn to standard electronic components, such as transistors, particularly those packaged in a standard DIP (dual-in-line) package configuration.

In the embodiment as illustrated in FIG. 2, two additional blind bores or blanks 44 are shown. They are used to symmetrically balance the loading on the module when it is secured an external pneumatic device. Depending on the specific flow configuration and the specific standard interface desired, these bores 44 could be provided with passageways therethrough to the opposite side of base layer 24 in order to provide fluid communication between an external pneumatic device and the internal components such as manifold 64 within module 10. Similarly, the invention permits the use of almost any number of inlets and outlets 18 and 20 and a wide variety of internal flow paths, as determined by the configuration of each of the various layers 13, 22, 24, 64, 80 within module 10.

Preferably, any desired additional passageways or variations in flow configuration will be provided at the time of manufacture, construction, or assembly of the module 10, in accordance with a predetermined design, in order to benefit from economies of scale in manufacturing large quantities of the selected standard module.

Figure 13:
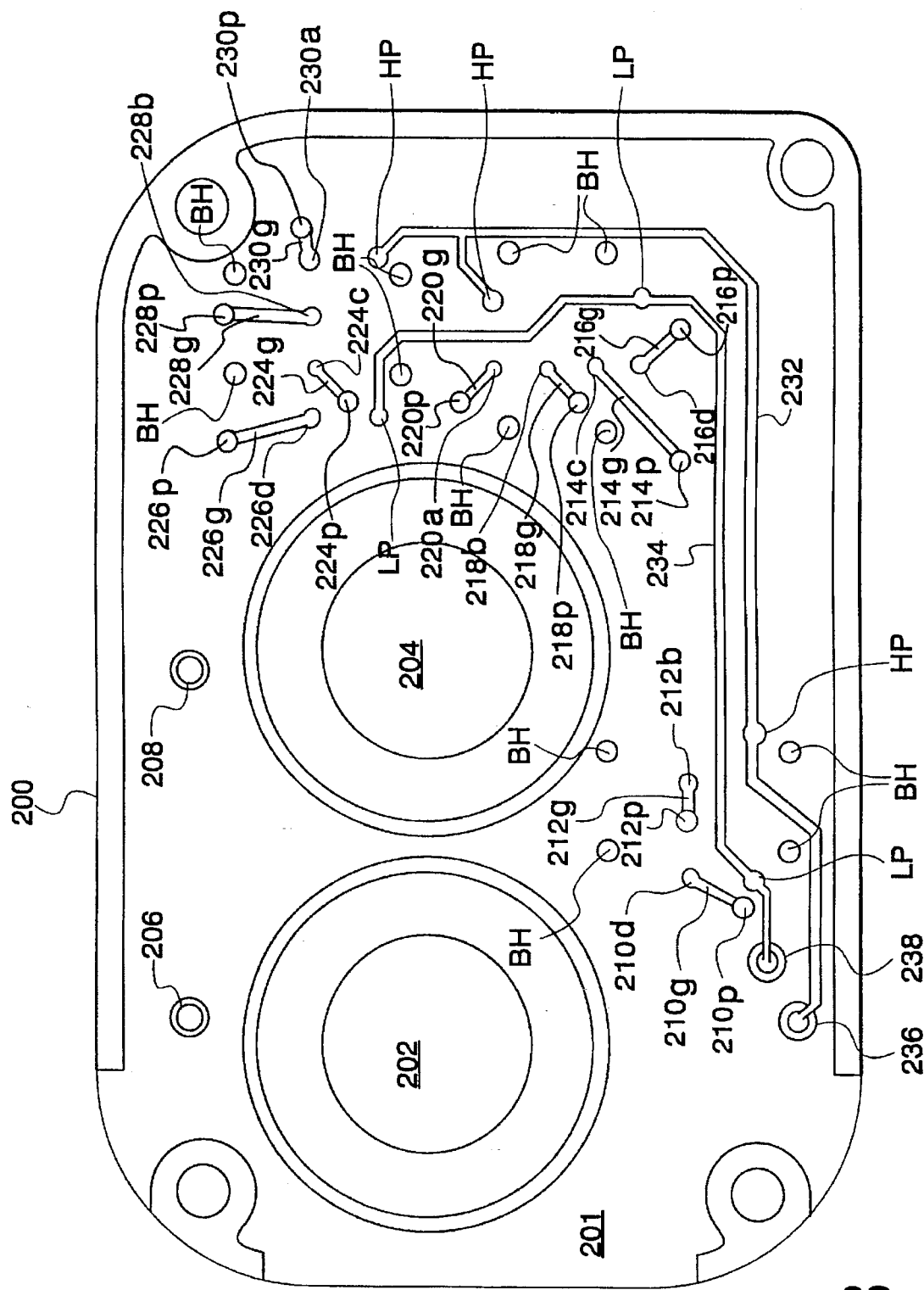
FIG. 13 is a rear elevational view of a piston body for a peritoneal dialysis system, the piston body being provided with passageways for delivering pneumatic signals for the control of a cassette forming a portion of a patient circuit.
Figure 14:
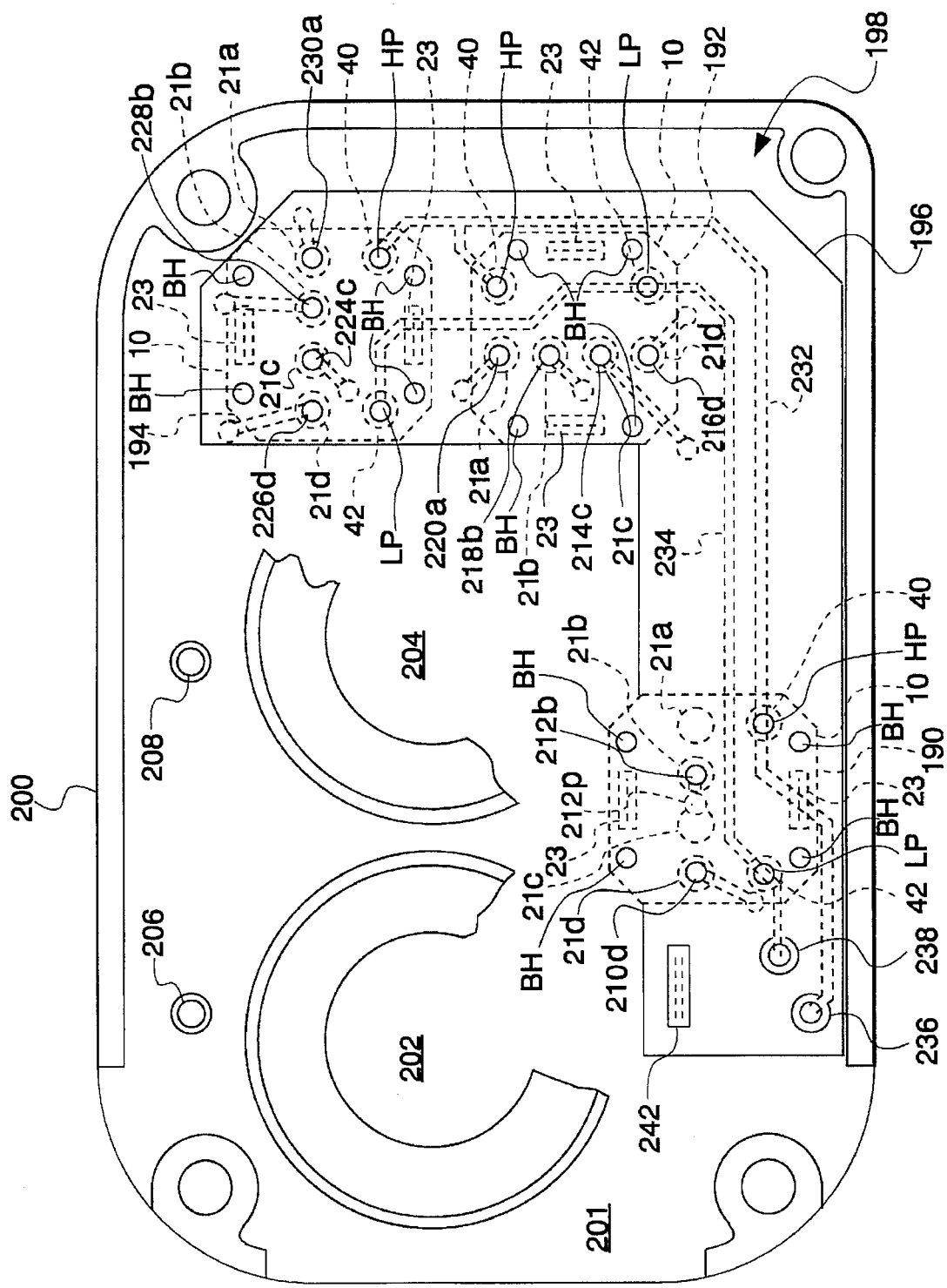
FIG. 14 is another rear elevational view of the piston body of FIG. 13, also showing a base plate and, in broken lines, the positioning of three electrofluidic modules and their fluidic, electrical, and mechanical connections to the base plate and the piston body.

The miniature electrofluidic module 10 may be used in a dialysis system or an electrofluidic dialysate handling system including a piston body 200, as may best be seen in FIGS. 13–15. The piston body 200 preferably is made of DELRIN (an acetyl compound), or another suitable material to withstand repeated stresses. The dialysate handling system is disclosed in more detail in U.S. Pat. No. 5,324,422 to Colleran, et al. and U.S. Pat. No. 5,350,357 to Kamen, et al., both of which patents are incorporated herein by reference as if fully reproduced herein.

As shown in FIGS. 13–15, a plurality of miniaturized electrofluidic modules 10, respectively numbered 190, 192, 194, are positioned on a base plate 196, forming a sealing connection over fluidic conducting lines or grooves 210g, 212g, 214g, 216g, 218g, 220g, 224g, 226g, 228g, 230g, 232, and 234, all of which grooves are formed in the piston body 200. The combination of the base plate or fixture 196 and electrofluidic modules 190, 192, and 194 is an electrofluidic assembly 198.

FIG. 13 shows the piston body 200 after said grooves have been machined. FIG. 14 shows base plate 196 mounted on the rear surface 201 of piston body 200, covering said grooves (shown in broken lines). Threaded bolt holes BH are tapped into the base plate and into the piston body 200, for receiving threaded bolts 54 to attach modules 190, 192, 194. The positions for said modules and their bottom surface bores 21a–d and electrical connectors 23 are shown in broken lines. Fluid passageways, e.g., for module 194, the passageways identified with reference numerals 230a, 228b, 224c, 226d, HP, and LP, are drilled through base plate 196, in order to permit fluids to communicate between the piston body 200 and each module. Similar passageways are provided for modules 190, 192. Finally, the modules are shown mounted on base plate 196 and piston body 200, FIG. 15.

The piston body 200 is used to pneumatically actuate a multi-component cassette (not shown) including two diaphragm pumps and ten liquid valves. The pump actuators 202, 204 receive pneumatic actuating signals through ports 206, 208, respectively. The ten liquid valves (not shown) are actuated by pneumatic signals transmitted through ten ports 210p, 212p, 214p, 216p, 218p, 220p, 224p, 226p, 228p, 230p. These ports extend from the rear of the piston body 200 (FIG. 13) to the piston front (not shown), where they deliver pneumatic signals to cause respective portions of a membrane in the cassette to seat or unseat and, thus, to actuate the respective liquid valves.

Formerly, each of the ten ports required a separate length of flexible plastic tubing extending from a remote housing where positive or negative pressure signals were selectively generated and transmitted through the separate tubes to the respective ports.

In accordance with one aspect of the invention, it is desired to provide only a single positive pressure line and a single negative pressure line into the piston body, along with electrical signals via a ribbon cable or the like, and to control the input of positive or negative pressure signals at the piston body itself. (The pump actuation and flow measurement operations may be conducted through the use of separate tubes, as before.)

In order to provide the desired positive and negative pressure signals to the ten valve-actuating ports, a positive pressure channel or groove 232 and a negative or subatmospheric pressure groove 234 are machined into the rear surface of the piston body 200 (FIG. 13). Connections or barbs 236 and 238 are provided for connection to external pressure and vacuum supplies, respectively.

The piston body 200 also is provided with standard interface connections in a predetermined geometry to mate with a selected standard electrofluidic module 10. Thus, mating receptacles a, b, c, d are machined into the piston body rear surface 201 for receiving connection to module inlets/outlets 20a, 20b, 20c, 20d, respectively, for as many such connections as may be desired. Herein, ports 230p, 228p, 224p, and 226p are connected via grooves 230g, 228g, 224g, and 226g to standard-positioned receptacles 230a, 228b, 224c, and 226d, respectively. Similarly, a relatively high pressure connection HP and a relatively low pressure connection LP are positioned for mating to standard module inlets or outlets 58, 60, respectively. Likewise, ports 220p, 218p, 214p, and 216p are connected via grooves 220g, 218g, 214g, and 216g to standard-positioned receptacles 220a, 218b, 214c, 216d, respectively. Finally, the ports 210p and 212p are connected via grooves 210g and 212g to receptacles 210d and 212 b.

Base plate 196 also is provided with a master electrical pin connector 240 for receiving electrical signals via a ribbon cable (not shown) for activating the microdevices 14. Circuit traces (not shown) are provided on the base plate 196 for connection to the individual module electrical pin connectors 23 for actuation of the total of twenty (20) valves 14 used in the three modules 190, 192, 194. The supply voltage may be about 3.5–5.0 VDC. This supply is provided via the ribbon cable and the circuit traces. The circuitry for base plate 196 may be similar to that shown for Fixture 250, see FIGS. 3 and 21, but with additional traces to accommodate the three modules 190, 192, 194. Preferably, the valves will be controlled by a bank of transistors or latched drivers (not shown), thereby limiting the number of lines needed for connection to an external controller. For example, BiMOS II 32-bit serial input latched drivers in a 44 lead plastic chip carrier, Model No. UCN-5833EP, available from Allegro Microsystems, may be used, as will be understood by those of ordinary skill in the art.

For each module 10, numbered as 190, 192, 194, the bottom of the module is provided with four inlet/outlet blind bores 21a–d which communicate with the internal parts of the module via inlet/outlets 20a–d, respectively (FIGS. 1–3). Each module also is provided with a blind pressure inlet bore 40 and blind vacuum outlet bore 42, which communicate to the internal parts of the module via pressure inlet channel 58 and vacuum outlet channel 60.

Each module 190, 192, 194 is mounted with bores 21a–d, 40, 42 in registration with the underlying and corresponding receptacles in the piston body. Thus, for module 190, bore 21d registers and communicates with receptacle 210d, and bore 21b registers and communicates with receptacle 212b. In module 190, blind bores 21a and 21c are not used. Blind pressure inlet bore 40 mates with pressure connection HP to communicate between the module 190 and pressure supply groove 232. Blind vacuum outlet bore 42 mates with vacuum connection LP to communicate between module 190 and low pressure groove 234.

Similarly, for module 192, module bores 21a, 21b, 21c, 21d, 40, and 42 mate with piston body receptacles 220a, 218b, 214c, 216d, HP, and LP, respectively. For module 194, module bores 21a, 21b, 21c, 21d, 40, and 42 mate with piston body receptacles 230a, 228b, 224c, 226d, HP, and LP, respectively.

It will be understood that base plate 196 is provided with holes or apertures (not shown) in registration with the piston body receptacles to permit communication with the module bores.

Thus, it will be observed that through the use of the electrofluidic module 10 and the electrofluidic assembly 198 of the invention, the ten liquid valve actuators incorporated into the piston body/cassette actuating device 200 may be actuated with only two external pneumatic supply lines (now shown), one for pressure and the other for vacuum, connected to barbs 236 and 238, respectively, instead of ten external supply lines as previously. Moreover, whereas the prior art required a remote manifold and valve system to select either pressure or vacuum signals for each supply line, the compact size of the modules 10 and assembly 198 permit the in situ selection of pressure or vacuum signals through the use of manifolds and valves immediately proximate to the liquid valve actuators, providing numerous advantages as discussed in the Summary of the Invention, supra.

Another example of the use of the miniaturized electrofluidic module 10 involves mounting upon a fixture 250, as may best be seen in FIGS. 20–21, comprising an electrical circuit board layer 252 having a pair of connectors 254 and 256 connected via a plurality of traces 260 to a set of bonding pads 262. The electrical connectors 254 and 256 connect with the module electrical connectors 23. A thin intermediate sheet 270 is positioned with a pair of positioning pins 274 and 276 with respect to a base layer 278 having a plurality of passages or grooves 280g, 282g, 284g, 286g, 288g, 290g, formed thereon. FIG. 19. Fluid communication can be effected through passageways 280p, 282p, 284p, 286p, 288p, 290p, through the grooves 280g, 282g, 284g, 286g, 288g, 290g associated with the respective passageways, and through ports provided in the gasketing material 270 to the electrical circuit board 252, and thence through corresponding passageways 252a, 252b, 252c, 252d, 252HP and 252LP to the corresponding bores 21a, 21b, 21c, 21d, 40, and 42, respectively, in module 10.

The bores in base layer 278 (FIG. 18), i.e., 280B, 284B, 290p, may be adapted for making connections to external fluidic tubes or the like. In the embodiment shown, bores 288p and 290p communicate with external connections through the top of base layer 278, while the other bores, such as bore 280B, communicate with external connections through the bottom of base layer 278. The mating connections may be made more durable or robust through the use of grooved inserts or barbs made from brass or other suitable materials.

The fixture 250 may be provided with four bolt holes 278BH in base layer 278, matching bolt holes in gasket layer 270, and similarly aligned bolt holes 252BH in circuit board 252. Threaded inserts 277 may be secured by press (interference) fit into the bolt holes to provide a secure and robust but releasable connection for threaded bolts 54, used to register and releasably mount module 10 onto fixture 250.

Thus, an electrofluidic assembly 198 may be comprised of one or more electrofluidic modules 10 mounted on a suitable fluidic fixture 250 or a base plate 196 on a fluidic piston body 200. In the preferred embodiment for use in an automated peritoneal dialysis system, the electrofluidic assembly 198 comprises three electrofluidic modules 10 mounted on a base plate 196 attached to fluidic piston body 200.

In this application, various electrofluidic assemblies are disclosed which may incorporate one or more electrofluidic modules, having advantages of easy installation and replacement of the modules. Generally, each module includes an electrofluidic member having a fluidic manifold and an electrical circuit.

As an alternative to modular construction, a simplified electrofluidic member may comprise an electrical circuit board having fluidic passageways therein, e.g., the circuit board 80 or the circuit board 252. The simplified electrofluidic member may be configured for mounting directly and perhaps permanently onto an underlying fluidic fixture, e.g., fixture 250 or piston body 200. Devices such as microvalves 14 may be mounted directly and permanently onto the electrofluidic member, and a return manifold may be placed over such devices and also be mounted directly onto the electrofluidic member. In the non-modular system, each component is mounted directly and perhaps permanently over the underlying components, preventing quick and easy replacement of defective components or groups. In particular, microvalves can be subject to failure and the need for replacement. In this alternative manner of construction, the assembly may comprise fewer layers, with possibly improved reliability due to fewer components, but the advantages of easy module installation and replacement may be lacking, due to the lack of standard mating fluidic, electrical, and mechanical interfaces provided by the preferred modular assembly.

Figure 23:
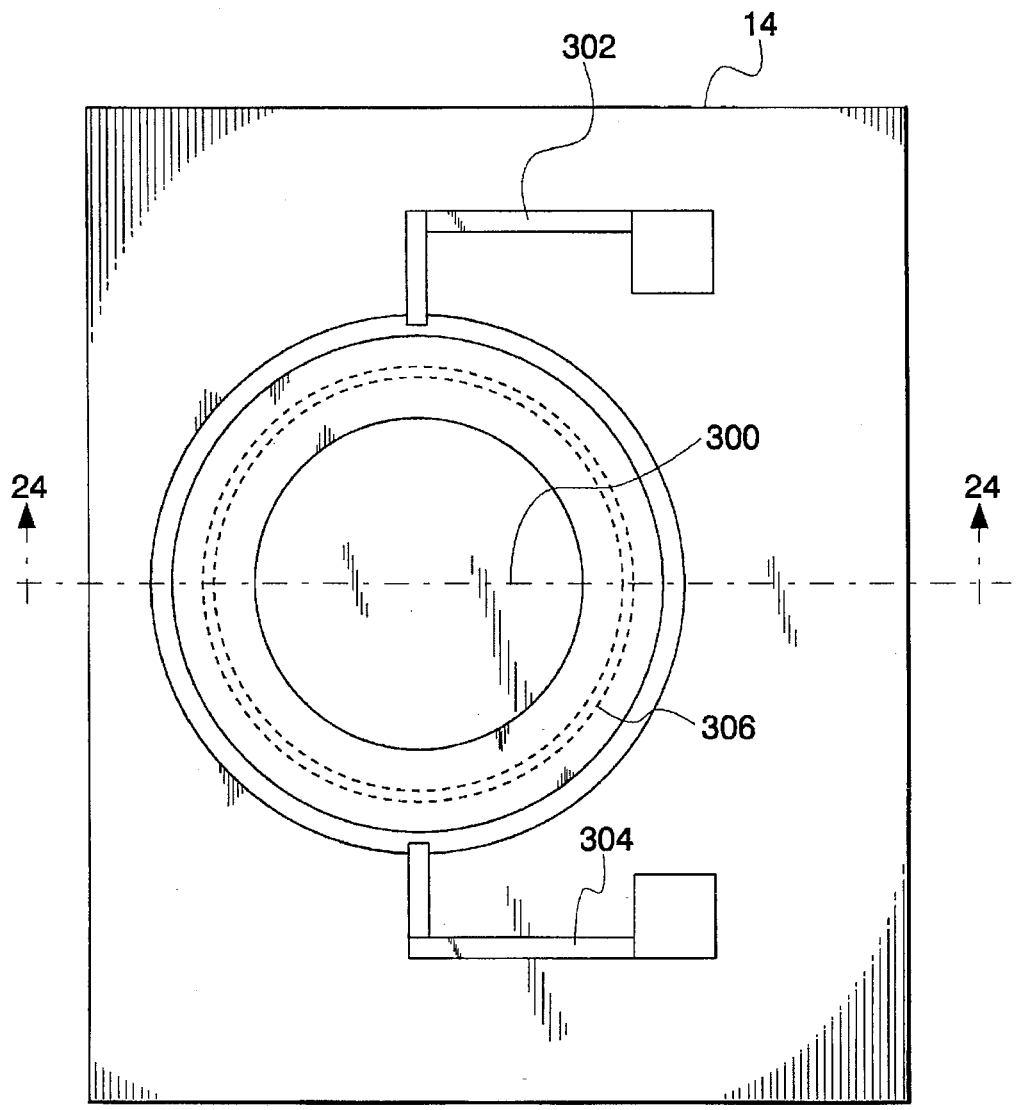
FIG. 23 is a plan view of a silicon micromachined valve.
Figure 24:
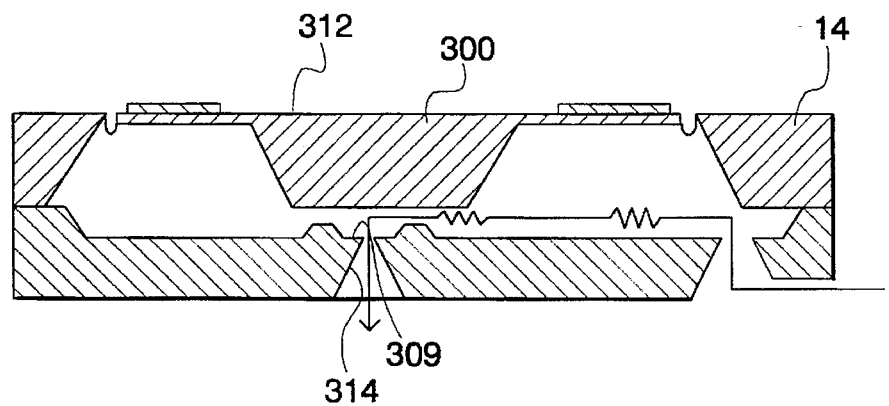
FIG. 24 is a section taken substantially along lines 24—24 of FIG. 23 showing details of the interior of the silicon micromachined valve.

It may be appreciated that each of the microactuators 14, as may best be seen in FIGS. 23 and 24, comprises a microvalve having a central boss 300, a pair of power leads 302 and 304 connected to a bridge region 306 near the boss 300 to effect movement of the boss 300 toward and away from a valve seat 309 to open and close the valve. It may be appreciated that the boss, when the valve 14 is closed, has a higher pressure applied to an upper surface 312 than is present at the passageway 314 directly connected to the valve seat, contributing to a bias-closed design for the preferably normally closed valve.

The microvalve may have very small dimensions, e.g., approximately 0.16×0.16×0.024 inch. The valve features proportional response, low power requirements, low cost, fast response, miniature size, a wide range of operating pressures up to about 25 to 30 psig. Each valve may be mounted on a printed circuit board 80 (FIG. 3) or the like.

Typical applications for the inventive module and assembly include I/P converters, pneumatic controls, respirators/ventilators, medical instrumentation, pressure regulators, flow controls, and analytical instruments.

The normally closed microvalve 14 used in module 10 offers proportional control of gas flows in the range of 0–250 cc/min. Large flows of up to about 1.5 liters/min. or more may be permitted with suitable modifications, e.g., by enlarging the clearances in the valve.

Batch fabricated using silicon micromachining technology, the microvalves 14 consist of a centrally bossed silicon diaphragm mated to an etched silicon valve body. An aluminum film is deposited on the diaphragm to form a bimetallic actuator. By varying the electrical power dissipated in resistors implanted in the diaphragm, and thus the temperature of the actuator, the thermal expansion difference between silicon and metal results in the controlled displacement of the central boss away from the valve seat.

Filters are recommended to keep particles from entering the module or valve chip, and a filtered, clean gas supply source is recommended.

Performance specifications for the microvalve 14, at 25° C. unless otherwise, may be as follows: The typical power requirement for each microvalve is 300–500 mW, the response time is about 100–200 msec (at 10 to 90% flow), the internal volume of the valve is about 0.12 cc, the operating voltage is about 3.5–5.0 VDC, the operating current is about 85–100 mA, the actuator resistance is about 40 ohm, the burst pressure limit is about 50 psi, and the back pressure limit is about 25 psi. Operating temperature range is +20° C. to +70° C., weight is about 0.3 gram, and recommended supply filtration is 25 microns. The above specifications are approximate, and are specific to the microvalve used in IC Sensors Model 4425. Other microactuators may be used in the module 10 without departing from the scope of the invention. Typical flow rates are 100–300 sccm for each open microvalve, but much greater flow rates are possible.

Moreover, due to the proximity of module 10 to the piston body 200 and thus to each liquid valve in the cassette (not shown), the response time of the liquid valve is less than about 100 msec, measured from the time an actuating electrical signal is sent to a microactuator 14 in module 10.

The size of module 10 may be about 1.0×1.0×7/16 inch. Each passageway within the module may have a diameter of about 1/16 inch, the bolt holes 25, 65, 81 may be slightly larger in diameter than the passageways, and the bores 40, 42, 44 may be about 3/32 inch in diameter.

In one embodiment of module 10, designed for a certain predetermined electrofluidic standard, the ports 20a–d are spaced about 6 mm apart, center to center, in a straight line. Inlets or outlets 18 are spaced about 8 mm from ports 20a and 20d, at right angles to (and both on the same side of) said straight line. Within each electrical pin connector 23, the pins may be spaced 1 mm apart, center to center, in a straight line. The line formed by the pins of one connector 23 may be parallel to and spaced about 21 mm from the line formed by the pins of the other connector 23. Each port 18, 20a–d may be about 1/16" in diameter.

The electrical traces on each of the circuit boards disclosed herein may be made of any suitable conductive material, but preferably are made of gold because of its excellent conductivity and non-corrosive properties.

The module 10 preferably is substantially flat and relatively planar, without lengthy protrusions vertically above the modular body. In its preferred embodiment, the module 10 may be described as a flat-pack.

Figure 25:
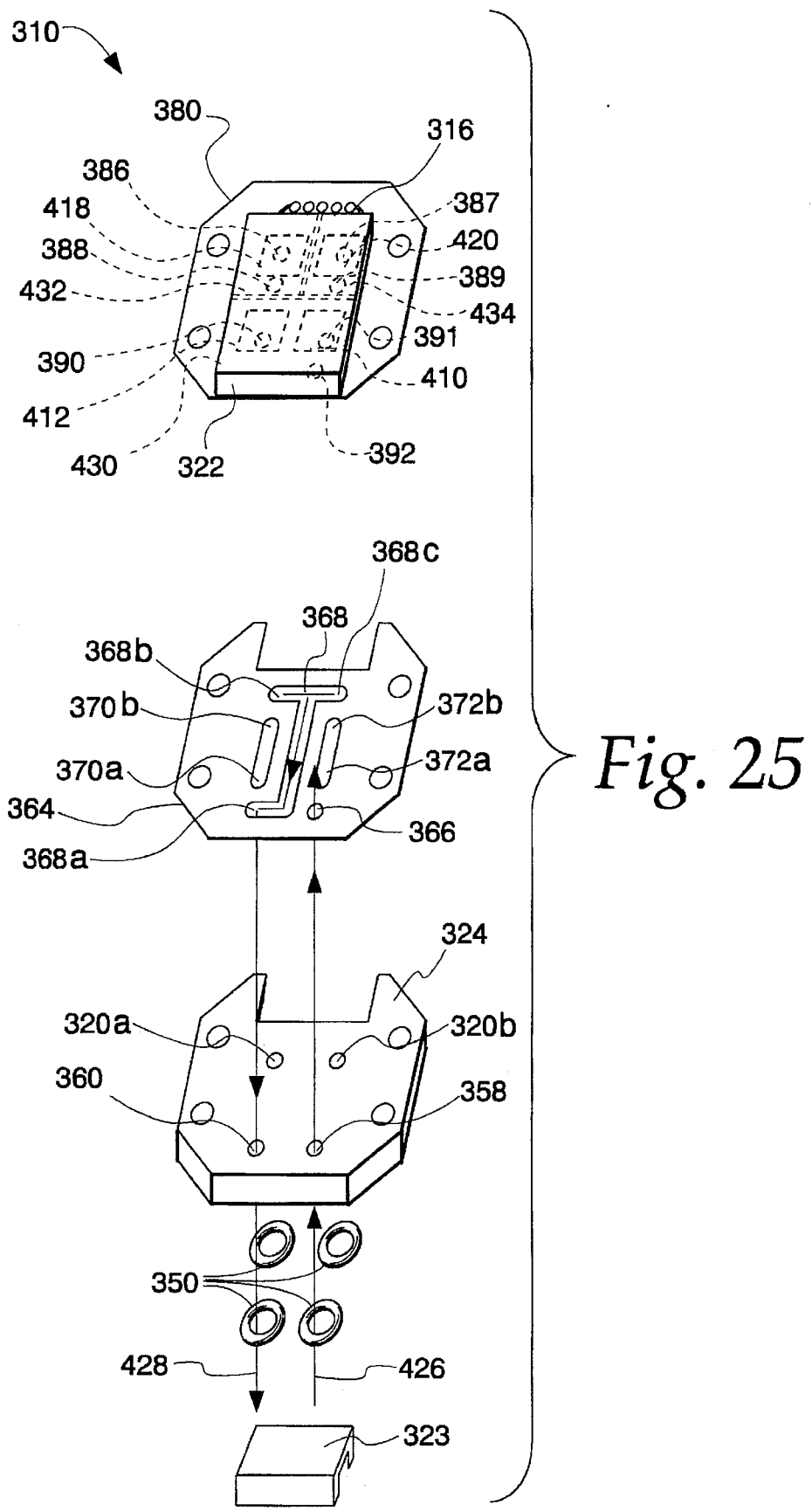
FIG. 25 is an exploded perspective view of an alternative embodiment of the electrofluidic module having four microvalves therein.

Four-valve electrofluidic module 310 is shown in FIG. 25. It includes a base layer 324, an intermediate manifold layer 364, an electrical layer 380, a device layer of microvalves 410, 412, 418, 420, and a return layer 322. The base 324 may receive an inlet of a pressurized gas stream 426 through an inlet 358, which is passed to a pressure slot 366. Pressure slot 366 communicates via slot 392 into a pressure manifolding section 430 of the return layer 322.

Manifold section 430 communicates pressure to the tops of two pressure-side microvalves 410, 412. Electrical signals can be transmitted via electrical traces 316 to open either or both of valves 410, 412 to transmit pressure downwardly and ultimately out through inlet/outlets 320b, 320a, respectively. For example, if valve 410 is opened, pressure will be transmitted to inlet/outlet slot end 372a, and then rearwardly to slot end 372b, downwardly to inlet or outlet passageway 320b, and out through the base layer 324, via an O-ring seal 350 for connection to a separate fixture.

Base 324 also is provided with a vacuum or subatmospheric exhaust passageway 360 for exhausting low pressure gas stream 428 to an external low-pressure system (not shown). Low pressure air may be drawn into either or both of the inlet/outlets 320a, 320b, by opening valves 418, 420, respectively. For example, if valve 418 is opened, low pressure air will be drawn into passageway 320a, upwardly to slot end 370b, upwardly through aperture 388 into vacuum manifold section 432, and downwardly through valve 418, into end 368b of h-shaped slot 368, laterally to end 368a, and down and out through vacuum exhaust outlet 360.

The system 310 also includes a pin connector 323 for coupling to electrical traces 316 on the electrical layer 380. Those traces are connected to the microvalves 410, 412, 418, 420 to control whether they are open or closed. A plurality of "O" rings 350 are mounted in bores in the underside of base 324 to form fluid-tight connections between the passageways 320a, 320b, 358, 360, and mating external connections. The operation of the four-valve embodiment 310 is substantially similar to that of the eight-valve electrofluidic module 10.

It will be observed that a four valve module 310 could be substituted for an eight valve module 10 in applications requiring only two fluidic inputs and two fluidic input/output ports, for example to replace eight valve module 190 (of which only four valves are used) as shown in FIGS. 14, 15, provided that the fixture 196, 200 is configured with fluidic, electrical, and mechanical interfaces to mate with the four valve module 310.

The claimed invention is not limited to the specific embodiments disclosed herein, but is defined by the appended claims and is intended to cover such alternative embodiments and uses as will be apparent to those of ordinary skill in the art, in the full spirit of the invention.

What is claimed is:

1. A miniature electrofluidic module for receiving a fluid and an electrical connection, said module comprising:

a substantially flat manifold layer having at least one fluidic inlet and an internal fluidic passageway connected to the inlet for receiving fluid;

a substantially flat electrical layer having a plurality of electrical layer fluidic passageways extending therethrough and connected to receive fluid from the internal fluidic passageway, the electrical layer having an electrical circuit comprising a plurality of individual micromachined device circuits thereon; and a substantially flat device layer having a plurality of micromachined devices thereon, each micromachined device being in electrical communication with one of the individual micromachined device circuits and in fluid communication with the respective electrical layer fluidic passageways to receive fluid therefrom.

2. A miniature electrofluidic module for receiving a fluid and an electrical connection, said module comprising:

a substantially flat first manifold layer having at least one fluidic inlet and an internal fluidic passageway connected to the inlet for receiving fluid;

a substantially flat electrical layer having an electrical circuit including circuit traces thereon, the electrical layer being positioned between the device layer and the first manifold layer, the electrical layer having fluidic passageways formed therein to allow fluid to flow from the first manifold layer and through the electrical layer;

a substantially flat micromachined device layer having a plurality of micromachined devices thereon in fluid communication with the fluidic passageway in the first manifold layer via the fluidic passageways in the electrical layer and in electrical communication with the electrical circuit on the electrical layer; and a second flat manifold layer having fluidic inputs and internal fluidic passageways, said second layer being disposed on a side of the micromachined device layer opposite from the side on which is located the first manifold layer for returning fluid flow to the first manifold layer.

3. A module in accordance with claim 2 wherein the first mentioned manifold layer has both fluidic inputs and outputs therein on one face of the module for flush mounting to a face of fixture.

4. A module in accordance with claim 1 wherein the electrical layer has an electrical trace thereon to form the electrical circuit; and connector elements are mounted on the module and are connected to the electrical trace and are adapted to be connected to other connectors leading to an electric controller.

5. A module in accordance with claim 1 wherein mechanical interface means of a predetermined configuration is provided for interfacing with a fixture to which the module is attached to properly position the module on the fixture.

6. A miniature electrofluidic module for receiving a fluid and an electrical connection, said module comprising:

a substantially flat first manifold layer having at least one fluidic inlet and an internal fluidic passageway connected to the inlet for receiving fluid;

a substantially flat electrical layer having an electrical circuit thereon;

a substantially flat device layer having a plurality of micromachined electrofluidic valves thereon in fluid communication with the fluidic passageway in the first manifold layer and in electrical communication with the electrical circuit on the electrical layer, wherein the device layer is a middle layer, the first manifold layer being disposed on a first side of the middle layer; and a second manifold layer disposed on an opposite side of the middle layer with fluidic passageways for returning fluid flow to the first manifold layer.

7. A miniature electrofluidic module for receiving a fluid and an electrical connection, said module comprising:

a substantially flat manifold layer having at least one fluidic inlet and an internal fluidic passageway connected to the inlet for receiving fluid;

a substantially flat electrical layer having an electrical circuit thereon;

a substantially flat device layer having a plurality of micromachined devices mounted side-by-side in a plane thereon in fluid communication with the fluidic passageway in the manifold layer and in electrical communication with the electrical circuit on the electrical layer, each of the micromachined devices comprising a valve member having an electrothermal member that displaces to modulate fluid flow with a change in electrical current applied thereto.

8. A miniature electrofluidic module for receiving a fluid and an electrical connection, said module comprising:

a substantially flat manifold layer having at least one fluidic inlet and an internal fluidic passageway connected to the inlet for receiving fluid, wherein the manifold layer comprises a first substrate having standard fluidic passageways arranged in a standard pattern, and a second substrate having fluidic passageways for further fluid distribution and in fluid communication with the standard fluidic passageways in the first substrate;

a substantially flat electrical layer having an electrical circuit thereon; and a substantially flat device layer having a plurality of micromachined devices thereon in fluid communication with the fluidic passageways in the manifold layer and in electrical communication with the electrical circuit on the electrical layer.

9. A module in accordance with claim 1 wherein the module comprises:

a flat-pack layered body having a flush mountable face on the manifold layer for flush mounting against a mating face of a fixture for aligning fluidically therewith; and electrical connectors on the flat-pack layered body directed toward the fixture to engage connectors on the fixture when the module is flush mounted against the fixture.

10. A miniature electrofluidic module having a fluidic inlet and an electrical connection, comprising:

a flat-pack, modular, layered body having a face;

an inlet/outlet manifold layer on the face having at least one inlet for inlet fluid flow in one direction and at least one outlet for return fluid flow in a return direction;

a plurality of micromachined devices in a middle layer of the body having fluidic passageways therein to modulate fluid flow;

an electrical layer in the body adjacent the micromachined devices having electrical circuits for operating the micromachined devices; and a return manifold on the modular body on the other side of the device layer to receive fluid flow from one part of the inlet/outlet manifold layer and to redirect the fluid flow to another part of the inlet/outlet manifold layer.

11. An electrofluidic module in accordance with claim 10 wherein a pair of electrical connectors are mounted on the modular body and are electrically connected to the electrical circuits for selective operation of the micromachined devices.

12. An electrofluidic module in accordance with claim 11 wherein the inlets and outlets are arranged in standard, predetermined positions for cooperation with a standard pattern of fluidic passageways in a fixture; and the electrical connectors being positioned in standard positions for mating with connectors on the fixture so that the module may be readily connected and disconnected with respect to the fixture.

13. A modular electrofluidic multiplexer for control of a fluid in response to electrical signals, comprising:

a substantially flat manifold layer having at least one fluidic inlet, an internal fluidic passageway connected to the inlet for receiving fluid flow therethrough;

a substantially flat electrical layer having a plurality of electrical layer fluidic passageways extending therethrough and connected to receive fluid from the internal fluidic passageway, the electrical layer having a plurality of individual micromachined actuator electrical circuit paths formed thereon for communication with a source of electrical signals;

a substantially flat, micromachined device layer having a plurality of micromachined actuators positioned thereon each micromachined actuator being in electrical communication with one of the individual micromachined actuator electrical circuit paths and in fluid communication with the respective electrical layer fluidic passageways to receive fluid therefrom; and a plurality of fluidic outlets coupled via fluidic outlet passages in fluid communication to the micromachined actuators so that in response to the electrical signals the micromachined actuators can selectively connect and disconnect the inlet from fluid communication with one or more of the outlet fluid paths.

14. An electrofluidic multiplexer in accordance with claim 13, wherein at least two of the micromachined actuators comprise micromachined valves.

15. An electrofluidic multiplexer in accordance with claim 14, wherein the micromachined valves each comprise a silicon micromachined valve.

16. An electrofluidic assembly having separable electrical and fluidic connections, said assembly comprising:

at least one electrofluidic module having a substantially flat manifold layer having at least one fluidic inlet and an internal fluidic passageway connected to the fluidic inlet for receiving fluid, a substantially flat electrical layer having a plurality of individual micromachined device electrical circuits and a plurality of electrical layer fluidic passageways in communication with the internal fluidic passageway, a substantially flat device layer having a plurality of micromachined devices thereon in fluid communication with the respective of the electrical layer fluidic passageways and in electrical communication with respective ones of the individual micromachined device electrical circuits;

the substantially flat manifold layer on the electrofluidic module having a fluidic interface located at a predetermined, standard position on one side of the module and having a fluidic passageway in fluid communication with the passageway in the electrofluidic device;

a first electrical connector on the module connected to the electrical circuit;

an electrofluidic circuit board having a standard, fluidic interface with a releasable mating connection with the standard fluidic interface of said module; and a second electrical connector on the electrofluidic circuit board for a releasable connection to the first electrical connector so that the electrofluidic module can be detachably connected to the electrofluidic circuit board.

17. An assembly in accordance with claim 16 wherein the fluidic interface on the fluidic manifold of each electrofluidic module has both fluidic inlets and outlets on a face of the module which is flush mounted against an opposing face of the electrofluidic circuit board.

18. An assembly in accordance with claim 16 wherein a plurality of electrofluidic devices are mounted in the electrofluidic module and separate electrical circuits are provided in the module for each of the electrofluidic devices, the first and second electrical connectors providing individual circuit connections for each of the electrofluidic devices.

19. A modular assembly in accordance with claim 16 wherein the electrofluidic device comprises a miniature, solenoid valve having fluid flow therethrough.

20. An assembly in accordance with claim 16 wherein the electrofluidic circuit board has electrical traces thereon, and a third electrical connector is connected to the traces to provide an electrical flow path to the connected first and second connectors.

21. An assembly in accordance with claim 16 further comprising releasable fastener means for detachably connecting the electrofluidic module to the electrofluidic circuit board.

22. An assembly in accordance with claim 20 wherein the releasable fastener means comprises at least one threaded bolt and one mating threaded groove.

23. An assembly in accordance with claim 16 wherein the electrofluidic module has a pop-in and pop-out connection with the electrofluidic circuit board to allow easy detachable mounting of the electrofluidic module.

24. In an electrofluidic system, the combination comprising:
   a fixture having fluidic passageways therein for the flow of a fluid;
   an electrofluidic member mounted on the fixture over the fixture passageways and having member passageways in fluid communication with the fixture passageways;
   a plurality of micromachined devices mounted on the electrofluidic member and having fluidic passageways connected to the inlets and outlets of the electrofluidic member;
   individual micromachined device electrical circuits on the electrofluidic member ones of which are respectively connected to the individual micromachined devices to operate the same to modulate fluid flow through the member passageways within the electrofluidic member; and
   return fluid flow directing means associated with the micromachined devices for directing fluid to return to the electrofluidic member.

25. An electrofluidic system in accordance with claim 24 wherein the return fluid flow directing means comprises a manifold member common to a plurality of micromachined devices.

26. An electrofluidic system in accordance with claim 24 wherein means permanently secures the micromachined devices to the electrofluidic member.

27. An electrofluidic system in accordance with claim 24 wherein an electrofluidic module contains a plurality of micromachined devices and the electrofluidic module is detachably connected electrically and fluidically to the electrofluidic member.

28. An electrofluidic system in accordance with claim 27 wherein the electrofluidic member comprises a printed circuit board having an electrical connector thereon for detachable connection to an electrical connector on the electrofluidic module.

29. In an electrofluidic system, the combination comprising:
   a fixture having fluidic passageways therein for fluid communication with other devices;
   an electrofluidic member mounted on the fixture and having member passageways mounted over the fixture passageways to communicate fluid flow with the other devices;
   an electrofluidic module on the electrofluidic member having a plurality of micromachined valves for modulating fluid flow between the module and the member;
   an electrical layer on the electrofluidic member having individual circuit paths for controlling the respective ones of the micromachined valves to modulate the fluid flow through the electrical layer; and
   an electrical connector on the electrofluidic module for connection to an electrical controller for operating the electrofluidic devices.

30. A system in accordance with claim 29 wherein the electrofluidic module has fluidic inlets and fluidic outlets in one face thereof flush mounted against the electrofluidic member; and the member and electrofluidic module have separable, interconnected electrical connectors.

31. A system in accordance with claim 29 wherein the electrofluidic devices comprise micromachined valves and wherein the module is provided with predetermined, standard fluidic inlets and outlets for matching with the member passageways.

32. In an electrofluidic system, the combination comprising:
   a fixture having fluidic passageways therein for fluid communication with other devices;
   a flat layer with fluidic inlets and outlets mounted over the passageways to communicate fluid flow to and from the other devices, the flat layer having circuit paths for controlling the electrofluidic micromachined valves to modulate the fluid flow;
   a plurality of electrofluidic micromachined valves thereon for modulating fluid flow among the inlets and outlets; and
   an electrical connector on the flat layer for electrical connection via a plurality of respective individual electrofluidic micromachined valve electrical circuits to the electrofluidic micromachined valves and to an electrical controller for operating the electrofluidic micromachined valves.

33. In an electrofluidic dialysate handling system, the combination comprising:
   a piston body having a plurality of valve actuators thereon and fluidic passageways in the piston body for fluid communication with the valve actuators;
   an electrofluidic member mounted on the piston body and having member passageways mounted over the body passageways to communicate fluid flow to the valve actuators;
   the electrofluidic member having a plurality of electrofluidic modules thereon for modulating fluid flow between the electrofluidic member and the modules;

an electrical layer on the electrofluidic member having circuit paths for controlling the respective electrofluidic modules to modulate the fluid flow; and an electrical connector on each of the electrofluidic modules for connection to an electrical controller for operating the electrofluidic devices.

34. A system in accordance with claim 33 wherein the electrofluidic modules each have fluidic inlets and fluidic outlets in one face thereof flush mounted against the electrofluidic member; and the electrofluidic member and electrofluidic modules have separable, interconnected electrical connectors.

35. A system in accordance with claim 33 wherein the modules each have at least one micromachined valve therein and the modules each have predetermined, standard fluidic inlets and outlets for matching with the member passageways.

36. In an electrofluidic dialysate handling system, the combination comprising:

a pneumatic cassette interface for supplying selected pneumatic control signals to a disposable cassette of a disposable dialysate delivery set to enable the disposable to deliver dialysate to a patient, the cassette interface having fluidic passageways therein for the flow of air;

an electrofluidic member mounted on the pneumatic cassette interface over the pneumatic cassette interface passageways and having member passageways in fluid communication with the pneumatic cassette interface passageways;

a plurality of micromachined valves mounted on the electrofluidic member and having fluidic passageways connected to the member passageways;

individual electrical circuits on the electrofluidic member connected to respective ones of the micromachined valves to operate the same to modulate air flow through the member passageways; and return fluid flow directing means associated with the micromachined devices for directing air to return to the electrofluidic member.

37. A system in accordance with claim 36 wherein the micromachined devices are mounted permanently on the electrofluidic member and the electrofluidic member is mounted permanently on the fixture.

* * * * *